US008404456B2

(12) United States Patent
Holgersson et al.

(10) Patent No.: US 8,404,456 B2
(45) Date of Patent: Mar. 26, 2013

(54) BLOOD GROUP ANTIGENS OF DIFFERENT TYPES FOR DIAGNOSTIC AND THERAPEUTIC APPLICATIONS

(75) Inventors: Jan Holgersson, Vastra Frolunda (SE); Jining Liu, Huddinge (SE); Linda Lindberg, Sollentuna (SE); Per Grufman, Huddinge (SE)

(73) Assignee: AbSorber AB, Stockholm (SE)

( * ) Notice: Subject to any disclaimer, the term of this patent is extended or adjusted under 35 U.S.C. 154(b) by 0 days.

(21) Appl. No.: 13/036,446

(22) Filed: Feb. 28, 2011

(65) Prior Publication Data

US 2011/0287556 A1 Nov. 24, 2011

Related U.S. Application Data

(62) Division of application No. 11/690,616, filed on Mar. 23, 2007, now Pat. No. 7,897,328.

(60) Provisional application No. 60/785,700, filed on Mar. 23, 2006.

(51) Int. Cl.
*G01N 33/00* (2006.01)
*G01N 1/18* (2006.01)

(52) U.S. Cl. ............ 435/7.25; 435/2; 435/7.1; 436/506; 436/507; 436/513; 436/518; 436/524; 436/527; 436/538; 436/10; 436/15; 436/175; 530/322; 530/402; 530/403; 530/387.3

(58) Field of Classification Search ............... 435/2, 7.1, 435/7.25, 7.92, 372; 436/506, 507, 512, 436/513, 518, 519, 523, 524, 527, 529, 533, 436/534, 538, 10, 175, 177, 15; 530/300, 530/322, 402, 403, 415, 387.3
See application file for complete search history.

(56) References Cited

U.S. PATENT DOCUMENTS

| 4,603,209 A | 7/1986 | Tsien et al. |
| 4,654,267 A | 3/1987 | Ugelstad et al. |
| 4,714,763 A | 12/1987 | Theodoropulos |
| 4,774,339 A | 9/1988 | Haugland et al. |
| 4,810,636 A | 3/1989 | Corey |
| 4,812,409 A | 3/1989 | Babb et al. |
| 4,849,362 A | 7/1989 | DeMarinis et al. |
| 4,981,977 A | 1/1991 | Southwick et al. |
| 5,132,432 A | 7/1992 | Haugland et al. |
| 5,187,288 A | 2/1993 | Kang et al. |
| 5,225,538 A | 7/1993 | Capon et al. |
| 5,242,805 A | 9/1993 | Naleway et al. |
| 5,248,782 A | 9/1993 | Haugland et al. |
| 5,268,486 A | 12/1993 | Waggoner et al. |

(Continued)

FOREIGN PATENT DOCUMENTS

| EP | 0274847 A2 | 7/1988 |
| EP | 1065250 A1 | 1/2001 |

(Continued)

OTHER PUBLICATIONS

Rydberg et al. In vitro assessment of a new ABO immunoabsorbent with synthetic carbohydrates attached to sepharose (Transpl. Int. 17: 666-672 (2005)—published online Nov. 17, 2004.*

(Continued)

*Primary Examiner* — Gail R Gabel
(74) *Attorney, Agent, or Firm* — Mintz Levin Cohn Ferris Glovsky and Popeo, P.C.; Ivor R. Elrifi; Cynthia A. Kozakiewicz

(57) ABSTRACT

The present invention provides compositions and methods for treating or preventing antibody mediated graft rejection and blood typing.

15 Claims, 12 Drawing Sheets

U.S. PATENT DOCUMENTS

| | | | |
|---|---|---|---|
| 5,274,113 A | 12/1993 | Kang et al. | |
| 5,334,708 A * | 8/1994 | Chang et al. | 530/391.5 |
| 5,428,130 A | 6/1995 | Capon et al. | |
| 5,433,896 A | 7/1995 | Kang et al. | |
| 5,451,343 A | 9/1995 | Neckers et al. | |
| 5,455,165 A | 10/1995 | Capon et al. | |
| 5,459,276 A | 10/1995 | Kuhn et al. | |
| 5,486,616 A | 1/1996 | Waggoner et al. | |
| 5,501,980 A | 3/1996 | Katerinopoulos et al. | |
| 5,514,582 A | 5/1996 | Capon et al. | |
| 5,516,946 A | 5/1996 | Jackson et al. | |
| 5,569,587 A | 10/1996 | Waggoner | |
| 5,569,766 A | 10/1996 | Waggoner et al. | |
| 5,627,027 A | 5/1997 | Waggoner | |
| 5,696,157 A | 12/1997 | Wang et al. | |
| 5,714,147 A | 2/1998 | Capon et al. | |
| 5,776,711 A | 7/1998 | Vyas et al. | |
| 5,808,044 A | 9/1998 | Brush et al. | |
| 5,830,912 A | 11/1998 | Gee et al. | |
| 5,877,310 A | 3/1999 | Reddington et al. | |
| 6,002,003 A | 12/1999 | Shen et al. | |
| 6,004,536 A | 12/1999 | Leung et al. | |
| 6,008,373 A | 12/1999 | Waggoner et al. | |
| 6,043,025 A | 3/2000 | Minden et al. | |
| 6,127,134 A | 10/2000 | Minden et al. | |
| 6,130,094 A | 10/2000 | Waggoner et al. | |
| 6,130,101 A | 10/2000 | Mao et al. | |
| 6,133,445 A | 10/2000 | Waggoner et al. | |
| 6,136,310 A | 10/2000 | Hanna et al. | |
| 6,162,931 A | 12/2000 | Gee et al. | |
| 6,229,055 B1 | 5/2001 | Klaubert et al. | |
| 6,339,392 B1 | 1/2002 | Ashihara | |
| 6,514,714 B1 * | 2/2003 | Lee et al. | 435/7.24 |
| 6,664,047 B1 | 12/2003 | Haugland et al. | |
| 6,686,457 B1 | 2/2004 | Nilsson | |
| 6,716,979 B2 | 4/2004 | Diwu et al. | |
| 6,974,873 B2 | 12/2005 | Leung et al. | |
| 6,977,305 B2 | 12/2005 | Leung et al. | |
| 2003/0073822 A1 | 4/2003 | Lofling et al. | |

FOREIGN PATENT DOCUMENTS

| | | |
|---|---|---|
| WO | WO-97/40104 A1 | 10/1997 |
| WO | WO-99/51702 A1 | 10/1999 |
| WO | WO-01/21624 A1 | 3/2001 |
| WO | WO-02/26891 A1 | 4/2002 |

OTHER PUBLICATIONS

Holgersson et al. Characteristics of protein-carbohydrate interactions as a basis of developing novel carbohydrate-based antirejection therapies, Immunology and Cell Biology 83: 694-708 (2005).*

Beverloo et al., "Immunochemical Detection of Proteins and Nucleic Acids on Filters Using Small Luminescent Inorganic Crystals as Markers", *Anal. Biochem.*, 203(2):326-334 (1992).

Clausen et al., "ABH and Related Histo-Blood Group Antigens; Immunochemical Differences in Carriers Isotypes and Their Distribution", *Vox Sang*, 56:1-20 (1989).

Davies et al., "Antibody-Antigen Complexes", *Annu. Rev. Biochem.*, 59:439-473 (1990).

Furukawa et al., "$A_1$ and $A_2$ Erythrocytes Can be Distinguished by Reagents That Do Not Detect Structural Differences Between the Two Cell Types", *J. Immunol.*, 135(6):4090-4094 (1985).

GenBank Accession No. Q10984 (Jul. 2007).
GenBank Accession No. Q10983 (Jul. 2007).
GenBank Accession No. Q10981 (Jul. 2007).
GenBank Accession No. AF455028 (Sep. 2003).
GenBank Accession No. NM-_000148 (Sep. 2007).
GenBank Accession No. P19526 (Aug. 2007).
GenBank Accession No. BAA11638 Feb. 2006).
GenBank Accession No. D82933 (Feb. 2006).
GenBank Accession No. NP_663625 (Nov. 2006).
GenBank Accession No. NM_145650 (Nov. 2006).
GenBank Accession No. CAD10625 (Apr. 2005).
GenBank Accession No. AJ417832 (Apr. 2005).
GenBank Accession No. XP_140694 (Oct. 2002).
GenBank Accession No. XM-_140694 (Oct. 2002).
GenBank Accession No. XP_006867 (Aug. 2002).
GenBank Accession No. XM_006867 Aug. 2002).
GenBank Accession No. NP_033177 (Jul. 2007).
GenBank Accession No. NM_009151 (Jul. 2007).

Holgersson et al., "Characteristics of protein-charbohydrate interactions as a basis for developing novel charbohydrate-based anti-rejection therapies", Immunol. Cell Biol., 83(6):694-708 (2005).

Liu et al., "Anti-Pig Anitbody Absorption Efficacy of α-Gal Carrying Recombinant P-Selectin Glycoprotein Ligand-1/Immunoglobulin Chimeras Increases With Core 2 β1,6-N-Acetylglucosaminyltransferase Expression", Glycobiol., 15(6):571-583 (2005).

Liu et al., "Removal of Xenoreactive Human Anti-Pig Antibodies by Absorption on Recombinant Mucin-Containing Glycoproteins Carrying the GALα1,3GAL Epitope", Transplan., 63(11):1673-1682 (1997).

Liu et al., "Multivalent Galα1,3Gal-Substitution Makes Recombinant Mucin-Immunoglobulins Efficient Absorbers of Anti-Pig Antibodies", Xenotransplan., 10(2):149-163 (2003).

Löfling et al., "Absorption of Anti-Blood Group A Antibodies on P-Selectin Glycoprotein Ligand-1/Immunoglobulin Chimeras Carrying Blood Group A Determinants: α1,2 Fucosyltransferases in Different Host Cells", Glycobiol., 12(3):173-182 (2002).

Malmqvist, M., "Biospecific Interaction Analysis Using Biosensor Technology", Nature, 361(6408):186-187 (1993).

Mammen et al., "Polyvalent Interactions in Biological Systems: Implications for Design and Use of Multivalent Ligands and Inhibitors", Angew. Chem. Int. Ed., 37:2754-2794 (1998).

Oriol et al., "A New Genetic Model Proposing That the *Se* Gene Is a Structural Gene Closely Linked to the *H* Gene", Am. J. Hum. Genet., 33:421-431 (1981).

Rydberg et al., "In Vitro Assessment of a New ABO Immuno-Sorbent with Synthetic Carbohydrates Attached to Sepharose", Tranpl. Int., 17(11):666-672 (2005).

Rydberg, L., "ABO-Incompatibility in Solid Organ Transplantation", Transfusion Med., 11(4):325-342 (2001).

Rydberg et al., "Characterization of the anti-A antibody binding an ABO-incompatible living donor renal transplantation", Nephrol. Dial. Transplan., 9(8):1162-1165 (1994).

Smith et al., "Single-Step Purification of Polypeptides Expressed in *Escherichia coli* as Fusions with Glutathione *S*-Transferase", Gene, 67(1):31-40 (1988).

Sonnenday et al., "Plasmapheresis, CMV Hyperimmune Globulin, and Anti-CD20 Allow ABO-Incompatible Renal Transplantation Without Splenectomy", Am. J. Transplant., 4:1315-1322 (2004).

Stegall et al., "ABO-Incompatible Kidney Transplantation", Transplan., 78(5):635-640 (2004).

Tanabe et al., "Removal of Anti-A/B Antibodies for Successful Kidney Transplantation Between ABO Blood Type Incompatible Couples", Trans. Sci., 17(3):455-462 (1996).

Tydén et al., "ABO Incompatible Kidney Transplantations Without Splenectomy, Using Antigen-Specific Immunoadsorption and Rituximab", Am. J. Transplan.., 5(1):145-148 (2005).

Tydén et al., "Successful ABO-Incompatible Kidney Transplantations Without Splenectomy Using Antigen-Speicific Immunoadsorption and Rituximab", Transplan., 76(4):730-743 (2003).

Warren et al., "Successful Renal Transplantation across Simultaneous ABO Incompatible and Positive Crossmatch Barriers", Am. J. Transplan., 4(4):561-568 (2004).

Welsh et al., "Transplantation of Blood Group A2 Kidneys Into O or B Recipients: The Effect of Pretransplant Anti-A Titers on Graft Survival", Transplan. Proc., 19(6):4565-4567 (1987).

Yamamoto, F., "Review: ABO Blood Group System—ABH Oligosaccharide Antigens, Anti-A and Anti-B, a and B Glycosyltransferases, and *ABO* Genes", Immunohematol., 20(1):3-22 (2004).

Takahashi, K., "Accomodation in ABO-Incompatible Kidney Transplantation: Why Do Kidney Grafts Survive?", Trans. Proc., 36(Suppl 25):193S-196S (2004).

Bensinger et al. "Immunoadsorption for Removal of A and B Blood-Group Antibodies." *N. Engl. J. Med.* 304.3(1981):160-162.

Bensinger et al. "In Vitro and in Vivo Removal of Anti-A Erthrocyte Antibody by Adsorption to a Synthetic Immunoadsorbent." *Transfusion*. 21.3(1981):335-342.

Bensinger et al. "Plasma Exchange and Plasma Modification for the Removal of Anti-Red Cell Antibodies Prior to Abo-Incompatible Marrow Transplant." *J. Clin. Apheresis*. 3.3(1987):174-177.

Bensinger et al. "Removal of Specific Antibody in Vivo by Whole Blood Immunoadsorption: Preliminary Results in Dogs." *J. Clin. Apheresis*. 1.1(1982):2-5.

Bensinger. "Plasma Exchange and Immunoadsorption for Removal of Antibodies Prior to ABO Incompatible Bone Marrow Transplant." *Artificial Organs*. 5.3(1981):254-258.

Rieben et al. "In Vitro Evaluation of the Efficacy and Biocompatibility of New, Synthetic ABO Immunoabsorbents." *Transplantation*. 60.5(1995):425-430.

\* cited by examiner

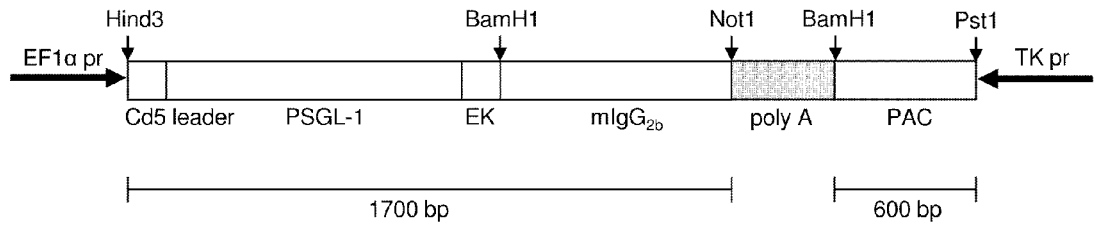
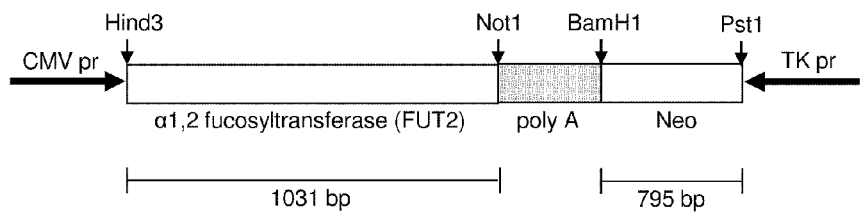
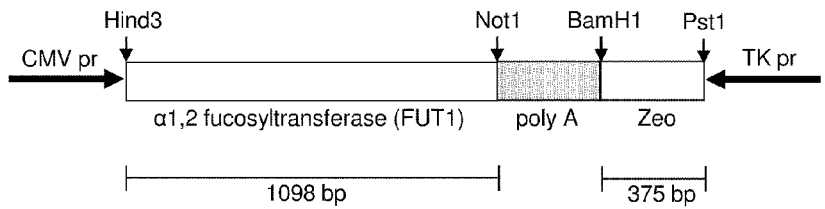
Figure 1A

CMV/GalNAcT/Bsd (A-gene)
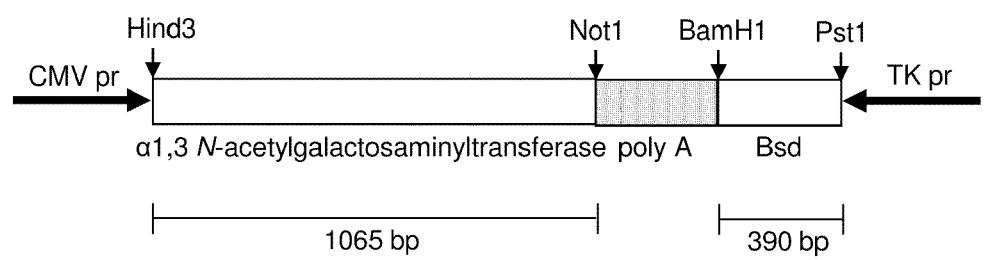
CMV/GalT/Bsd (B-gene)
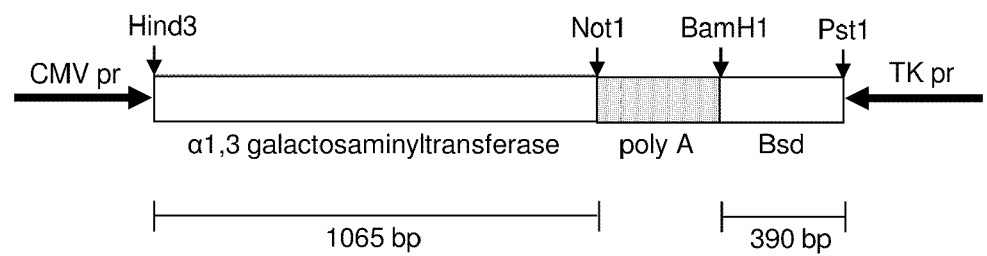
Figure 1B

EF1α/β1,6GlcNAcT/Neo (core 2)
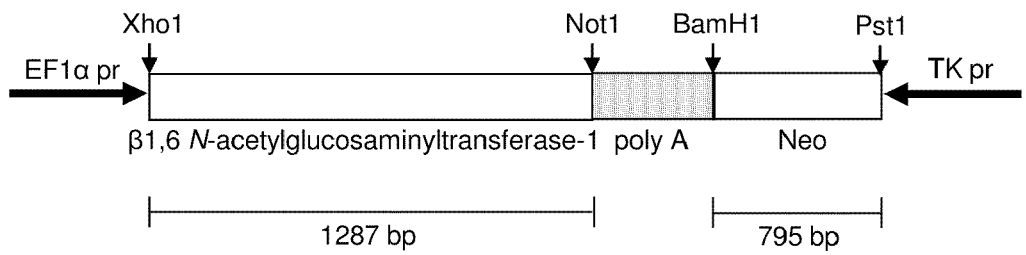
CMV/β1,3GlcNAcT/Zeo (core 3)
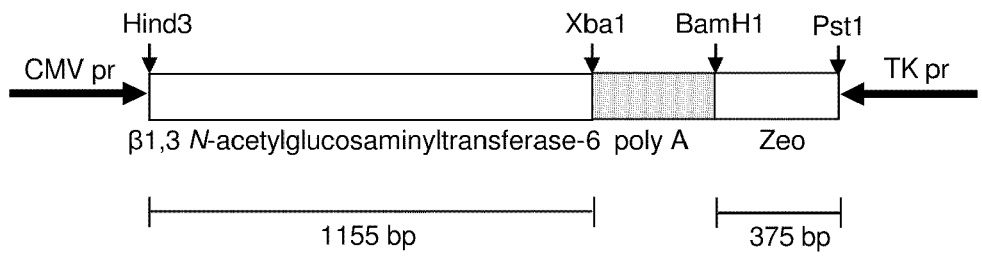
CMV/GalT5/GPT
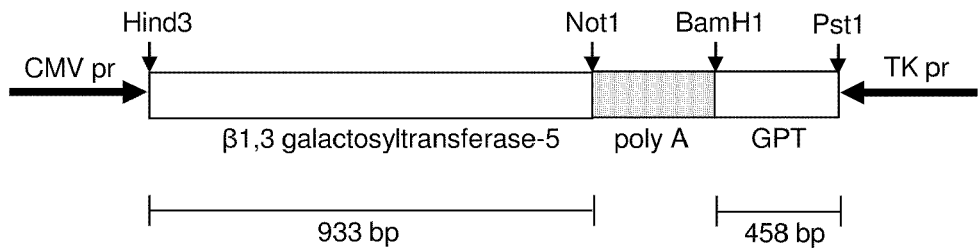
Figure 1C

CHO-K1 cells

Tested beads from the left
Red 6 um
Plain 7 um
Blue 7 um

Tested beads from the left
Red 6 um
Plain 7 um
Blue 7 um

BLOOD GROUP ANTIGENS OF DIFFERENT TYPES FOR DIAGNOSTIC AND THERAPEUTIC APPLICATIONS

RELATED APPLICATIONS

This application is a divisional of U.S. Ser. No. 11/690,616 filed Mar. 23, 2007, (now U.S. Pat. No. 7,897,328, issued on Mar. 1, 2011), which claims priority to 60/785,700 filed Mar. 23, 2006, the contents of which are incorporated herein by reference in their entireties.

INCORPORATION OF SEQUENCE LISTING

The contents of the text file named "23254-512D01US_ST25.txt," which was created on May 3, 2011 and is 803 bytes in size, are hereby incorporated by reference in their entirety.

FIELD OF THE INVENTION

The invention relates to generally to compositions and methods for treating or preventing antibody-mediated graft rejection and more particularly to compositions including blood group determinants useful for removing anti-blood group antigen antibodies.

BACKGROUND OF THE INVENTION

Renal transplantation across the ABO barriers was found, already in the early days of transplantation, to result in a high incidence of transplants that never functioned, and it was therefore regarded as a prerequisite in allotransplantation to comply with the traditional Landsteiner rules used for blood transfusion. The recipient's preformed anti-A/B isoagglutinins are responsible for hyperacute rejection of ABO-incompatible grafts. This hyperacute rejection is similar to that seen in alloimmunized patients with donor-reactive HLA-antibodies. The first trial to cross the ABO barrier in transplantation was started in the early 1970's grafting blood group $A_2$ cadaveric kidneys to 0 recipients.[1] In the 1980's, using $A_1$ and B donors Alexandre performed the first series of ABO incompatible living donor (LD) renal transplantations and obtained graft survival similar to those of ABO compatible cases. The immunosuppressive protocol encompassed pre-operative plasmapheresis to remove anti-A/B antibodies, donor platelet transfusion, splenectomy and induction therapy with anti-lymphocyte/thymocyte globulin, injection of blood group A or B substances extracted from porcine stomach and Cyclosporine-Azathioprine-prednisone. Since then, more than 500 cases of ABO incompatible LD renal transplantations have been reported worldwide, mainly from Japan (reviewed in[1]), and the importance of reducing recipient anti-A/B antibody levels before grafting to avoid rejection has been well documented.[2,3] The graft survival in these series is good (1 year graft survival of about 85% for $A_1$ and B donors) but slightly inferior to that of ABO compatible grafts due to single cases with severe anti-A/B antibody mediated rejection.[4,5] Recent data on ABO incompatible renal transplantations using an anti-CD20 antibody (Rituximab) combined with antibody removal were shown to be even better with regard to graft survival[6,7].

In times of severe organ shortage, an increased use of grafts from ABO incompatible donors will allow more LD kidney transplantations to be performed. In addition, the experience gained in this field will also be applicable on the pre-treatment and post-transplant management of HLA-sensitized patients.[8]

SUMMARY OF THE INVENTION

The invention is based in part on improved compositions and method for removing blood group antigen antibodies form plasma and a method of blood typing.

In one aspect the invention provides a composition containing a least two blood group antigens were each blood group antigen is expressed on different core saccharide chain type. Preferably composition contains 2, 3, 4, 5, 6, 7, 8, 9, 10, 11 or more blood group A/B antigens.

In another aspect, the presence of blood group antibodies in a sample form a subject is determined (e.g. blood typing) by providing a collection of microbeads of different subtypes, where each subtype is coated with a different blood group antigen and adding the sample from the subject to said collection of microbeads. The sample and microbeads are incubated for sufficient time for anti-blood group antibodies in the sample to bind to blood group antigens on the microbeads to form an anti blood group antibody-microbead complex. The complex is incubated, e.g. contacted with at least one labeled ligand capable of specifically binding with said anti-blood group antibodies bound to the blood group antigens and the presence of labeled ligand bound to the anti-blood group antibodies is detected to determine the presence or absence of said reactive antibodies. The ligand is for example an antibody or fragment thereof. The antibody is a monovalent antibody fragment, such as a Fab or a Fab' fragment. For example the Fab or Fab' fragment is an anti-Fc antibody fragment, an anti-kappa light chain antibody fragment, an anti-lambda light chain antibody fragment, and a single chain antibody fragment. The label is for example a fluorescent label. Labeled ligand is detected by methods known in the art such as flow cytometry or luminex.

Blood group reactive antibodies in a sample are removed by comprising by providing a collection of microbeads of different subtypes, where each subtype is coated with a different blood group antigen. The sample is contacted with the collection of microbeads and incubated for sufficient time for anti-blood group antibodies in the sample to bind to the blood group antigens. The microbeads and the sample is separated thereby removing the blood group reactive antibodies from the sample Blood group antigens include A antigen, B antigen and H antigen. Core saccharide chain types include type 1, type 2, type 3 and type 4. The blood group antigens are free saccharides (referred to herein as ABO oligosaccharide or optionally the blood group antigen are expressed on a mucin polypeptide. The mucin polypeptide is part of a mucin immunoglobin fusion protein (referred to herein as ABO fusion protein or polypeptides)

Optionally, ABO oligosaccharide or ABO fusion proteins are linked, e.g. covalently or non-covalently to a solid support such as microbeads. The microbeads are for example latex. By microbeads of a different subtype is meant that the microbeads differ from one another by size, color or both. The range in diameter is from about 2 µm to about 15 µm. Preferably, the microbead is approximately 5 µm in diameter. Most preferably, the microbeads are approximately 5 µm in diameter.

The sample is for example, whole blood, serum or plasma.

In some aspects, the compositions are formulated as an absorber for the removal of blood group antibodies from whole blood or plasma. Also provided by the invention is a collection of microbeads of different subtypes, wherein each subtype is coated with different blood group antigen. For example, the collection contains as microbeads of at least 2, 3, 4, 5, 6, 7, 8, 9, 10, 20, 25, 30, 40, 50 or more different subtypes.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIGS. 1A shows schematic representations of the EF1α/PSGL-1/mIgG$_{2b}$/PAC, CMV/FUT2/Neo (Se-gene), and CMV/FUT1/Zeo (H-gene) vectors used to produce the fusion proteins carrying blood group antigens.

FIG. 1B shows schematic representations of the CMV/GalNAcT/Bsd (A-gene) and CMV/GalT/Bsd (B-gene) vectors used to produce the fusion proteins carrying blood group antigens.

FIG. 1C shows schematic representations of EF1α/(β1,6GlcNAcT/Neo (core 2), CMV/β1,3GlcNAcT/Zeo (core 3), and CMV/GalT5/GPT vectors used to produce the fusion proteins carrying blood group antigens.

FIG. 5A shows a flow cytometry of beads tested under FSC-H spectra.

FIG. 5B shows a flow cytometry of beads tested under FL2-H spectra.

FIG. 5C shows a flow cytometry of beads tested under FSC-H spectra.

FIG. 5D shows a flow cytometry of beads tested under FL2-H spectra.

DETAILED DESCRIPTION OF THE INVENTION

Figure 2:
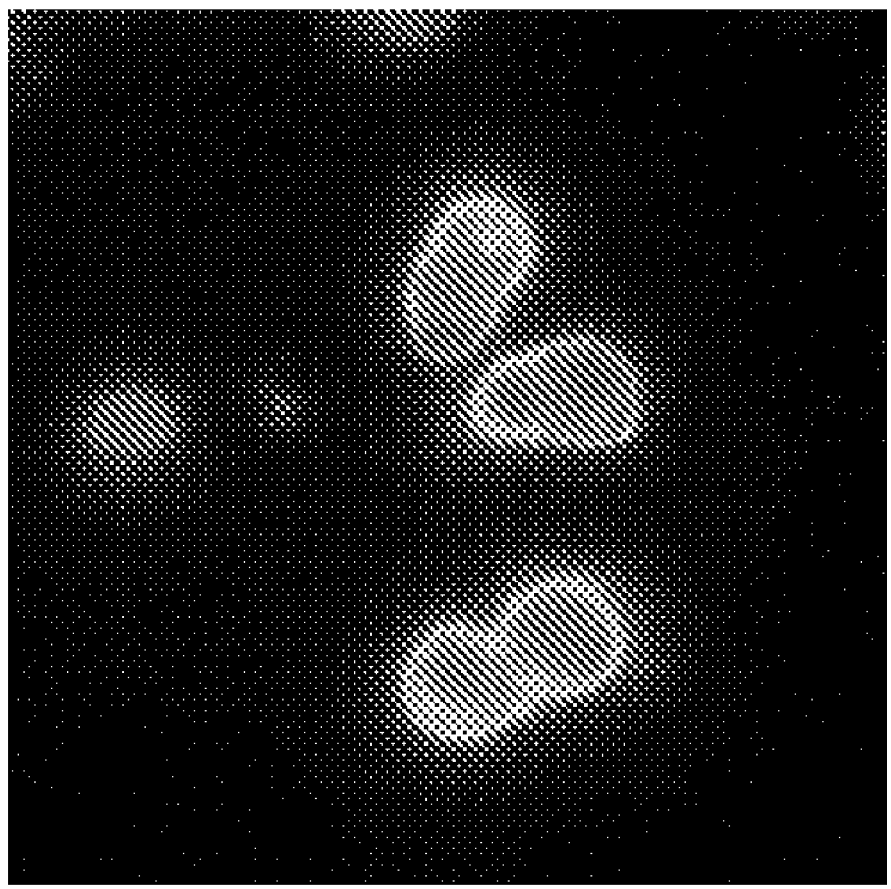
FIG. 2 is a photograph showing the cellular localization of PSGL-1/mIgG2b, which was determined by indirect immunofluorescence. PSGL-1/mIgG2b protein was detected using a FITC-conjugated goat anti-mouse IgG Fc antibody (Sigma) diluted 1:200 in blocking buffer. Cell nuclei were stained with 4,6-diamidino2-phenylindole (DAPI).
Figure 3:
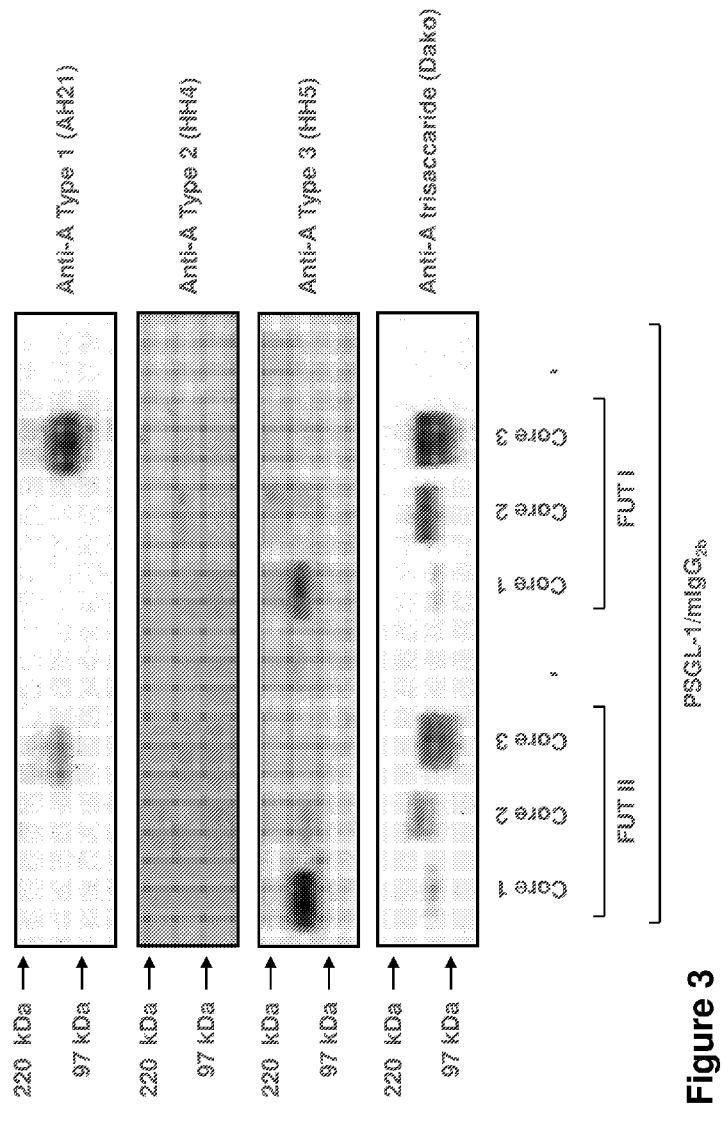
FIG. 3 is a photograph of a Western Blot showing blood group A determinants carrying different outer core chains.
Figure 4:
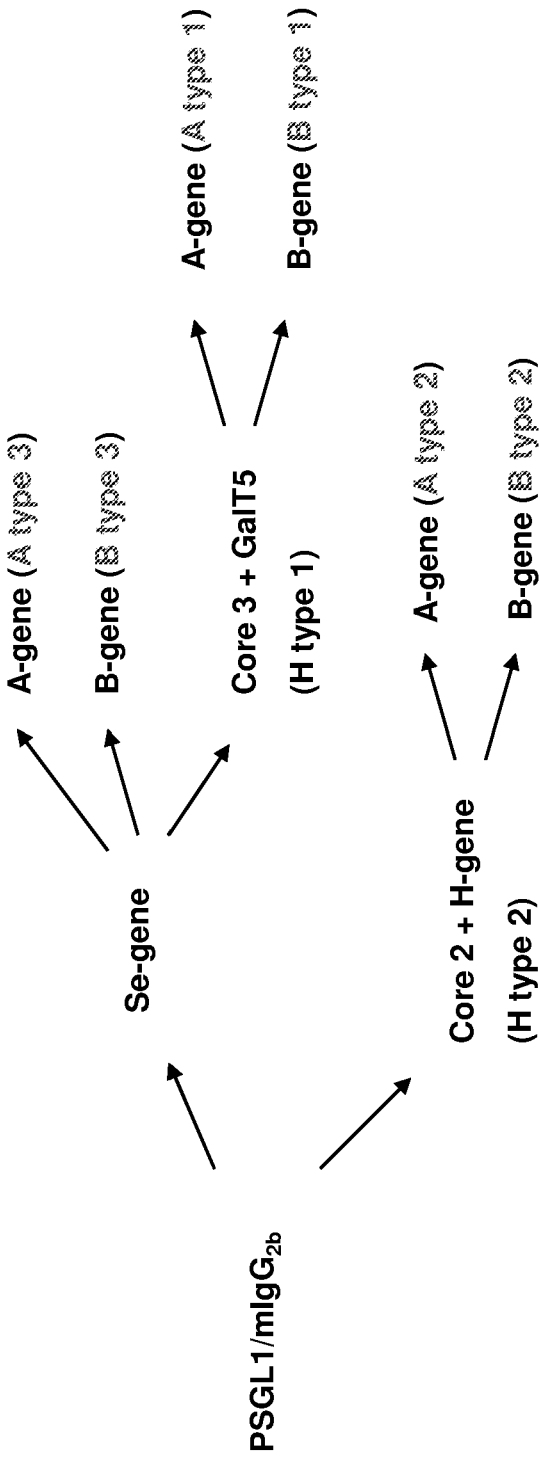
FIG. 4 is a schematic representation of the ABH transfection scheme to produce ABO fusion peptides on different glycan precursors.

The invention is based in part in the discovery that blood group epitopes can be specifically expressed at high density and by different core saccharides chains (e.g. type 1, type 2, type 3 or type 4) as either free saccharides or on mucin-type protein backbones. It has been discovered that using blood group antigens carried by the different core saccharides chains when used in combination are more efficient at removing anti-blood group antibodies from blood prior to transplantation. Additionally, the compositions of the invention are useful diagnostically and prognostically to determine the presence of blood group reactive antibodies in a subject.

In one aspect the invention provides a composition contains at least two different blood group antigens (i.e., oligosaccharides) where each blood group antigen is expressed a different core saccharide chain (i.e., glycan precursors). These oligosaccharides are referred to herein as "ABO oligosaccharides". The blood group antigens are free saccharide. Alternatively, the blood group antigen is expressed on a mucin polypeptide. For example, the blood group antigen is expressed in a mucin immunoglobulin fusion proteins (referred to herein as "ABO fusion proteins") The ABO fusion proteins carries an epitope specific for a blood group determinants. For example, the ABO fusion protein carries either the A epitope, the B epitope or the H epitope. Alternatively, the ABO fusion protein carries two epitope for blood group antigens. For example the ABO fusion protein carries both the A and B epitope. In some aspects the ABO fusion protein carries all three epitopes (i.e., A, B and H). The ABO fusion proteins of the invention expresses the A, B, or H epitope on different glycan precursors, e.g., type 1, type 2 or type 3 precursor chains.

Optionally, the ABO oligosaccharides or the ABO fusion proteins are linked to a solid support to allow for separation of blood group antigens from blood.

Accordingly, the ABO oligosaccharides and ABO fusion protein are useful in eliminating recipient anti-blood group ABO antibodies from blood or plasma prior to for example, an ABO incompatible organ, bone marrow transplantation or in order to make universal donor plasma. The ABO oligosaccharides or ABO fusion protein absorbs 50%, 60%, 70%, 80%, 90%, 95%, 98% or 100% of anti-blood group ABO antibodies from recipient blood or plasma.

The ABO oligosaccharide is more efficient on a carbohydrate molar basis in removing or binding anti-blood group antibodies as compared blood group oligosaccharide expressed on a single core saccharide chain. The ABO oligosaccharide binds 2, 4, 10, 20, 50, 80, 100 or more-fold greater number of anti-blood group antibodies as compared to an equivalent amount of free saccharides expressed on a single core saccharide chain.

Similarly, the ABO fusion peptide is more efficient on a carbohydrate molar basis in removing or binding anti-blood group antibodies as compared free saccharides of wild type AB determinants. The ABO fusion peptide binds 2, 4, 10, 20, 50, 80, 100 or more-fold greater number of anti-blood group antibodies as compared to an equivalent amount of free saccharides of wild type AB determinants.

The ABO oligosaccharides and ABO fusion proteins are also useful in a method of blood typing. The methods of the invention are superior to current blood typing methods as it allows quantification of blood group antibodies of different classes and subclasses. In particular it allows for the detection of chain-type specific antibodies. This is clinically relevant as the immune system can respond specifically to blood group antigens on different core chains. Moreover blood group antigens on different core chains are expressed in a cell and tissue specific manner. Thus, by allowing the detection of chain specific antibodies will allow for better donor-recipient cross matching in ABO incompatible organ allografts, which will decrease hyperacute rejection ABH Histo-Blood Group Antigens The ABH antigen are found on almost all cells in the human body, but their physiological role, if any, remains an unresolved issue. They are of carbohydrate nature and are built up by different glycosyltransferases, i.e. enzymes adding monosaccharide units in a sequential manner to the non-reducing end of the growing oligosaccharide chain. Oligosaccharides can be carried by proteins or lipids,[9] or can be found free in body fluids (e.g. breast-milk)[9]

The ABH antigens are divided into subgroups, depending on the inner core saccharide chain.[9] As an example, both A, B and H antigens are expressed on type 1 (Galβ1,3GlcNAc), type 2 (Galβ1,4GlcNAc), type 3 (Galβ1,3GalNAcα) and type 4 (Galβ1,3GalNAcβ) chains. Type 4 chain ABH antigens are only found lipid-bound. H antigens are produced by the addition of a fucose in an α1,2 linkage to the different core chains containing a terminal galactose. Both A and the B antigens are produced from subtypes of H by addition of an N-acetylgalactosamine (A) or a galactose (B) in an α1,3 linkage to the terminal galactose. The glycosyltransferases responsible for the biosynthesis of A and B antigens require the presence of the α1,2-fucose for addition of the terminal N-acetylgalactosamine and galactose, respectively.

Two structurally distinct α1,2-fucosyltransferases enables the biosynthesis of the H antigen as initially described by Oriol.[10] One is encoded by the H locus (FUT-I) and the other by the secretor (Se) locus (FUT-II). The FUT-I gene product is responsible for erythrocyte H antigen expression and acts predominantly on type 2 chains, but activity towards type 1 chains has also been shown. In contrast, the FUT-II gene product is expressed by salivary gland acinar cells as well as epithelial cells lining the gastrointestinal, reproductive and pulmonary tracts, and acts mainly on type 1 chains but probably also on type 3 and 4 chains.

The gene products responsible for A and B antigen expression have been shown to have a common origin.[11] Mutations leading to the substitution of four amino acid residues in the A as compared to the B encoded gene product result in a shift in the donor sugar nucleotide preference from UDP-N-acetylgalactosamine to UDP-galactose. The serologically named O phenotype lacks expression of both of these gene products due to a frame shift mutation in the original A allele, and hence do not express A or B determinants.[11] The blood group A has been subdivided into serologically distinct groups, the most frequent subgroups being $A_1$ and $A_2$.[12] These A subtypes are produced by two different α1,3-N-acetylgalactosaminyltransferases, one with a preference for H type 3 and 4 antigens ($A_1$) and the other with a preference for H type 1 and 2 ($A_2$) antigens.

The Importance of Multivalency

Protein-carbohydrate interactions are generally characterized by a low affinity of binding. Although this may seem irrational, it provides the basis for a fast on/off rate that is essential under physiological conditions as it allows for fast, highly changeable interactions to occur between cell receptors, antibodies and other carbohydrate binding proteins and their glycosylated ligands. Higher affinities, when needed, are in nature accomplished by the use of multivalency. The binding of several receptors on one biological entity to several carbohydrate ligands on another, can result in a 10-10 000 fold increase of the affinity. Examples of polyvalent interactions include the binding of microbes (viruses, bacteria or bacterial toxins) to a cell surface, cell-cell binding, and binding of polyvalent molecules, such as antibodies, to a cell surface[13] Inhibition of polyvalent interactions with monovalent inhibitors is usually ineffective even if the binding activity of the inhibitor has been structurally optimized. Accordingly, a number of different molecules (e.g. polyacrylamide, peptides, bovine serum albumin, dendrimers and cyclodextrins) have been used as backbones for multiple presentations of mono- and oligosaccharides attempting to create multivalent binding of the corresponding receptors.[13] An alternative approach involves non-covalent association of the ligand with the head groups in liposomes, membranes or other surfaces.[13] The success of these glycoconjugates varies, but in general the affinity is enhanced 10- to 1000-fold as compared to the monovalent interactions. The nanomolar activities most often characterizing physiological protein-carbohydrate interactions has been achieved in a few cases[13] by optimising ligand presentation (i.e. ligand structure, degree of valency, backbone structure and intra/inter-ligand distances), i.e. nature's way of presenting the carbohydrate was mimicked in as much detail as possible.

Recombinant Mucins with Tailored Glycan-Substitution as Efficient Absorbers of Anti-Carbohydrate Antibodies.

Mucin-type proteins are normally found at mucosal surfaces and are characterized by their abundant O-glycan substitution (every second to third amino acid). Up to 50% of their molecular weight is due to the carbohydrate substitution. By co-expressing various glycosyltransferase cDNAs with the mucin-Ig they can determine the structures of its O-glycans such that it carries several copies of biologically significant carbohydrate determinants. In this way, mucins carrying blood group A determinants have been made and shown to bind anti-blood group A Abs with high efficacy[1]. In fact, mucin-based absorbers of anti-blood group A antibodies were shown to be approximately a 100 times more efficient (as calculated on the number of blood group A determinants) in binding anti-A antibodies than the blood group A trisaccharide linked via a spacer directly to agarose beads (this is the arrangement of Glucosorb®). This, is explained by the fact that several copies of the A determinant is expressed with for Ab-binding optimal spacing on one mucin-type carrier protein'. Likewise, recombinant mucins carrying the carbohydrate epitope, Galα1,3Gal (α-Gal), have been shown to be very efficient absorbers of anti-Gal antibodies; the main hurdle preventing successful pig-to-man xenotransplantation[15-17]. Thus, mucins are very efficient scaffolds for optimal presentation of bioactive carbohydrates.

The Importance of Blood Group Antigen Subtypes

As described above, blood group ABH determinants can be carried by different core saccharide chains. These have a cell- and tissue-specific distribution in the human body, and the importance of the individual ABH antigens as target molecules for anti-blood group ABH antibodies is not known. Similarly, it is not known whether the anti-blood group ABH antibody repertoire is heterogeneous, i.e. whether subpopulations of these antibodies can distinguish between the different subtypes of ABH antigens and actually require more of the carbohydrate chain than the terminal trisaccharide for binding. Some data suggests that it is sufficient to use only the A or B trisaccharide for adsorption of all antibodies specific for blood group A or B antigens, respectively, indicating that this would be true also for detection of these antibodies[19-20]. However the data of the present invention show that it is possible to obtain more efficient antibody adsorption and detection using different subtypes (i.e. carried by different core saccharide chains) of the ABH blood group antigens.

Oligosaccharides with Tailored Core Saccharide Chains as Efficient Absorbers of Anti-Carbohydrate Antibodies.

Following from the discussion above, a mixture of mucin-type fusion proteins or oligosaccharides carrying the ABH determinants on different core saccharide chains (to obtain structural heterogeneity) will adsorb a broader repertoire of anti-A/B antibodies. Using different combinations of glycosyltransferase genes, the mucin-immunoglobulin fusion protein can be engineered to carry several copies of O-linked glycans with defined inner and outer core saccharide chains. These can be further elongated with the ABH determinants. Thus, recombinant technology can be used to make structurally diverse blood group A or B mucins, which can be used to adsorb a broad repertoire of anti-A or -B antibodies.

Blood Group Antigen Oligosaccharides

In various aspects the invention provides blood group antigen oligosaccharides. Blood group antigens include (A, B, and O (H). The blood group antigens are specific for all the blood group subtypes. By blood group subtypes it is meant that the blood group antigens are expressed on different core saccharide chain types. Core saccharides chain types include type-, type-2, type 3 and type-4 glycan precursors.

Exemplary blood group antigen oligosaccharides include the following:

Blood group A antigens on types 1-4

A type 1 GalNAcα1,3(Fucα1,2)Galβ1,3GlcNAcβ1-R

A type 2 GalNAcα1,3(Fucα1,2)Galβ1,4GlcNAcβ1-R

A type 3 GalNAcα1,3(Fucα1,2)Galβ1,3GalNAcα1-R

A type 4 GalNAcα1,3(Fucα1,2)Galβ1,3GalNAcβ1-R

Blood group B antigens on types 1-4

B type 1 Galα1,3(Fucα1,2)Galβ1,3GlcNAcβ1-R

B type 2 Galα1,3(Fucα1,2)Galβ1,4GlcNAcβ1-R

B type 3 Galα1,3(Fucα1,2)Galβ1,3GalNAcα1-R

B type 4 Galα1,3(Fucα1,2)Galβ1,3GalNAcβ1-R

Wherein R represents the mucin, when the blood group antigen is carried on a fusion protein, the point of attachment when the oligosaccharide is linked to a solid support, or nothing when the oligosaccharide is a free saccharide.

Fusion Polypeptides

In various aspects the invention provides fusion proteins that include a first polypeptide containing at least a portion of a glycoprotein, e.g., a mucin polypeptide operatively linked to a second polypeptide. As used herein, a "fusion protein" or "chimeric protein" includes at least a portion of a mucin polypeptide operatively linked to a non-mucin polypeptide. A "mucin polypeptide" refers to a polypeptide having a mucin domain. The mucin polypeptide has one, two, three, five, ten, twenty or more mucin domains. The mucin polypeptide is any glycoprotein characterized by an amino acid sequence substituted with O-glycans. For example a mucin polypeptide has every second or third amino acid being a serine or threonine. The mucin polypeptide is a secreted protein. Alternatively, the mucin polypeptide is a cell surface protein.

Mucin domains are rich in the amino acids threonine, serine and proline, where the oligosaccharides are linked via N-acetylgalactosamine to the hydroxy amino acids (O-glycans). A mucin domain comprises or alternatively consists of an O-linked glycosylation site. A mucin domain has 1, 2, 3, 5, 10, 20, 50, 100 or more O-linked glycosylation sites. Alternatively, the mucin domain comprises or alternatively consists of an N-linked glycosylation site. A mucin polypeptide has 50%, 60%, 80%, 90%, 95% or 100% of its mass due to the glycan. A mucin polypeptide is any polypeptide encoded for by a MUC gene (i.e., MUC1, MUC2, MUC3, etc.) Alternatively, a mucin polypeptide is P-selectin glycoprotein ligand 1 (PSGL-1), CD34, CD43, CD45, CD96, GlyCAM-1, MAdCAM or red blood cell glycophorins. Preferably, the mucin is PSGL-1. Whereas a "non-mucin polypeptide" refers to a polypeptide of which at least less than 40% of its mass is due to glycans.

Within an ABO fusion protein of the invention the mucin polypeptide can correspond to all or a portion of a mucin protein. In one embodiment, an ABO fusion protein comprises at least a portion of a mucin protein. "At least a portion" is meant that the mucin polypeptide contains at least one mucin domain (e.g., an O-linked glycosylation site). In one embodiment, the mucin protein comprises the extracellular portion of the polypeptide. For example, the mucin polypeptide comprises the extracellular portion of PSGL-1.

The first polypeptide is glycosylated by one or more blood group transferases. The first polypeptide is glycosylated by 2, 3, 5 or more blood group transferases. Glycosylation is sequential or consecutive. Alternatively glycosylation is concurrent or random, i.e., in no particular order. For example the first polypeptide is glycosylated by a α1,2 fucosyltransferase, such as the H- or Se-gene encoded α1,2 fucosyltransferases. Exemplary α1,2 fucosyltransferases are FUT1 (Gen Bank Acc. Nos: Q10984; O10983; O10981; AT455028 and NM00148) and FUT2. (Gen Bank Acc. No: P19526; BAA11638; D82933 and A56098) Alternatively, the first polypeptide is glycosylated by 1,3 N-acetylgalactosaminyltransferase or α1,3 galactosaminyltransferase. In some aspects, the first polypeptide is glycosylated by both an α1,2 fucosyltransferase and a 1,3 N-acetylgalactosaminyltransferase or a α1,3 galactosaminyltransferase.

Within the fusion protein, the term "operatively linked" is intended to indicate that the first and second polypeptides are chemically linked (most typically via a covalent bond such as a peptide bond) in a manner that allows for O-linked glycosylation of the first polypeptide. When used to refer to nucleic acids encoding a fusion polypeptide, the term operatively linked means that a nucleic acid encoding the mucin polypeptide and the non-mucin polypeptide are fused in-frame to each other. The non-mucin polypeptide can be fused to the N-terminus or C-terminus of the mucin polypeptide.

In a further embodiment, the ABO fusion protein may be linked to one or more additional moieties. For example, the ABO fusion protein may additionally be linked to a GST fusion protein in which the ABO fusion protein sequences are fused to the C-terminus of the GST (i.e., glutathione S-transferase) sequences. Such fusion proteins can facilitate the purification of ABO fusion protein. Alternatively, the ABO fusion protein may additionally be linked to a solid support. Various solid supports are known to those skilled in the art. Such compositions can facilitate removal of anti-blood group antibodies. For example, the ABO fusion protein is linked to a particle made of, e.g., metal compounds, silica, latex, polymeric material; a microtiter plate; nitrocellulose, or nylon or a combination thereof. The ABO fusion proteins linked to a solid support are used as an absorber to remove anti-blood group antibodies from a biological sample, such as blood or plasma.

In another embodiment, the fusion protein is includes a heterologous signal sequence (i.e., a polypeptide sequence that is not present in a polypeptide encoded by a mucin nucleic acid) at its N-terminus. For example, the native mucin signal sequence can be removed and replaced with a signal sequence from another protein. In certain host cells (e.g., mammalian host cells), expression and/or secretion of polypeptide can be increased through use of a heterologous signal sequence.

An chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, for example, Ausubel et al. (eds.) CURRENT PROTOCOLS IN MOLECULAR BIOLOGY, John Wiley & Sons, 1992). Moreover, many expression vectors are commercially available that encode a fusion moiety (e.g., an Fc region of an immunoglobulin heavy chain). A glycoprotein Ibα encoding nucleic acid can be cloned into such an expression vector such that the fusion moiety is linked in-frame to the immunoglobulin protein.

ABO fusion polypeptides may exist as oligomers, such as dimers, trimers or pentamers. Preferably, the ABO fusion polypeptide is a dimer.

The first polypeptide, and/or nucleic acids encoding the first polypeptide, can be constructed using mucin encoding sequences are known in the art. Suitable sources for mucin polypeptides and nucleic acids encoding mucin polypeptides include GenBank Accession Nos. NP663625 and NM145650, CAD10625 and AJ417815, XP140694 and XM140694, XP006867 and XM006867 and NP00331777 and NM009151 respectively, and are incorporated herein by reference in their entirety.

In some embodiments, the mucin polypeptide moiety is provided as a variant mucin polypeptide having a mutation in the naturally-occurring mucin sequence (wild type) that results in increased carbohydrate content (relative to the non-mutated sequence). For example, the variant mucin polypeptide comprised additional O-linked glycosylation sites compared to the wild-type mucin. Alternatively, the variant mucin polypeptide comprises an amino acid sequence mutations that results in an increased number of serine, threonine or proline residues as compared to a wild type mucin polypeptide. This increased carbohydrate content can be assessed by determining the protein to carbohydrate ratio of the mucin by methods known to those skilled in the art.

In some embodiments, the mucin polypeptide moiety is provided as a variant mucin polypeptide having mutations in the naturally-occurring mucin sequence (wild type) that results in a mucin sequence more resistant to proteolysis (relative to the non-mutated sequence).

In some embodiments, the first polypeptide includes full-length PSGL-1. Alternatively, the first polypeptide comprise less than full-length PSGL-1 polypeptide such as the extracellular portion of PSGL-1. For example, the first polypeptide may be less than 400 amino acids in length, e.g., less than or equal to 300, 250, 150, 100, 50, or 25 amino acids in length. Exemplary PSGL-1 polypeptide and nucleic acid sequences include GenBank Access No: XP006867; XM006867; XP140694; and XM140694.

The second polypeptide is preferably soluble. In some embodiments, the second polypeptide includes a sequence that facilitates association of the ABO fusion polypeptide with a second mucin polypeptide. In preferred embodiments, the second polypeptide includes at least a region of an immunoglobulin polypeptide. "At least a region" is meant to include any portion of an immunoglobulin molecule, such as the light chain, heavy chain, FC region, Fab region, Fv regions or any fragment thereof. Immunoglobulin fusion polypeptides are known in the art and are described in e.g., U.S. Pat. Nos. 5,516,964; 5,225,538; 5,428,130; 5,514,582; 5,714,147; and 5,455,165.

In some embodiments, the second polypeptide comprises a full-length immunoglobulin polypeptide. Alternatively, the second polypeptide comprises less than full-length immunoglobulin polypeptide, e.g., a heavy chain, light chain, Fab, $Fab_2$, Fv, or Fc. Preferably, the second polypeptide includes the heavy chain of an immunoglobulin polypeptide. More preferably the second polypeptide includes the Fc region of an immunoglobulin polypeptide.

In another aspect of the invention the second polypeptide has less effector function that the effector function of a Fc region of a wild-type immunoglobulin heavy chain. Fc effector function includes for example, Fc receptor binding, complement fixation and T cell depleting activity. (See for example, U.S. Pat. No. 6,136,310.) Methods of assaying T cell depleting activity, Fc effector function, and antibody stability are known in the art. In one embodiment the second polypeptide has low or no affinity for the Fc receptor. In an alternative embodiment, the second polypeptide has low or no affinity for complement protein C1q.

Another aspect of the invention pertains to vectors, preferably expression vectors, containing a nucleic acid encoding mucin polypeptides, or derivatives, fragments, analogs or homologs thereof. In various aspects the vector contains a nucleic acid encoding a mucin polypeptide operably linked to an nucleic acid encoding an immunoglobulin polypeptide, or derivatives, fragments analogs or homologs thereof. Additionally, the vector comprises a nucleic acid encoding a blood group transferase such as a α1,2 fucosyltransferase, a α1,3 N acetylgalactosamininytransferase, a α1,3 galactosyltransferase or any combination thereof. The blood group transferase facilitates the addition of blood group determinants on the peptide backbone of the mucin portion of the ABO fusion protein. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell).

The term "regulatory sequence" is intended to include promoters, enhancers and other expression control elements (e.g., polyadenylation signals). Such regulatory sequences are described, for example, in Goeddel, GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., ABO fusion polypeptides, mutant forms of ABO fusion polypeptides, etc.).

The recombinant expression vectors of the invention can be designed for expression of ABO fusion polypeptides in prokaryotic or eukaryotic cells. For example, ABO fusion polypeptides can be expressed in bacterial cells such as *Escherichia coli*, insect cells (using baculovirus expression vectors) yeast cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988. *Gene* 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion *E. coli* expression vectors include pTrc (Amrann et al., (1988) *Gene* 69:301-315) and pET 11d (Studier et al., GENE EXPRESSION TECHNOLOGY: METHODS IN ENZYMOLOGY 185, Academic Press, San Diego, Calif. (1990) 60-89).

One strategy to maximize recombinant protein expression in *E. coli* is to express the protein in host bacteria with an impaired capacity to proteolytically cleave the recombinant protein. See, e.g., Gottesman, GENE EXPRESSION TECHNOLOGY: METHODS IN ENZYMOLOGY 185, Academic Press, San Diego, Calif. (1990) 119-128. Another strategy is to alter the nucleic acid sequence of the nucleic acid to be inserted into an expression vector so that the individual codons for each amino acid are those preferentially utilized in *E. coli* (see, e.g., Wada, et al., 1992. *Nucl. Acids Res.* 20: 2111-2118). Such alteration of nucleic acid sequences of the invention can be carried out by standard DNA synthesis techniques.

In another embodiment, the ABO fusion polypeptide expression vector is a yeast expression vector. Examples of vectors for expression in yeast *Saccharomyces cerivisae* include pYepSec1 (Baldari, et al., 1987. *EMBO J.* 6: 229-234), pMFa (Kurjan and Herskowitz, 1982. *Cell* 30: 933-943), pJRY88 (Schultz et al., 1987. *Gene* 54: 113-123), pYES2 (Invitrogen Corporation, San Diego, Calif.), and picZ (InVitrogen Corp, San Diego, Calif.).

Alternatively, ABO fusion polypeptide can be expressed in insect cells using baculovirus expression vectors. Baculovirus vectors available for expression of proteins in cultured insect cells (e.g., SF9 cells) include the pAc series (Smith, et al., 1983. *Mol. Cell. Biol.* 3: 2156-2165) and the pVL series (Lucklow and Summers, 1989. *Virology* 170: 31-39).

In yet another embodiment, a nucleic acid of the invention may be expressed in mammalian cells using a mammalian expression vector. Examples of mammalian expression vectors include pCDM8 (Seed, 1987. *Nature* 329: 840) and pMT2PC (Kaufman, et al., 1987. *EMBO J.* 6: 187-195). When used in mammalian cells, the expression vector's control functions are often provided by viral regulatory elements. For example, commonly used promoters are derived from polyoma, adenovirus 2, cytomegalovirus, and simian virus 40. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, glycoprotein Ibα fusion polypeptides can be expressed in bacterial cells such as *E. coli*, insect cells, yeast or mammalian cells (such as human, Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (MOLECULAR CLONING: A LABORATORY MANUAL.

2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding glycoprotein Ibα fusion polypeptides or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) ABO fusion polypeptides. Accordingly, the invention further provides methods for producing ABO fusion polypeptides using the host cells of the invention. In one embodiment, the method comprises culturing the host cell of invention (into which a recombinant expression vector encoding ABO fusion polypeptides has been introduced) in a suitable medium such that ABO fusion polypeptides is produced. In another embodiment, the method further comprises isolating ABO polypeptide from the medium or the host cell.

The ABO fusion polypeptides may be isolated and purified in accordance with conventional conditions, such as extraction, precipitation, chromatography, affinity chromatography, electrophoresis or the like. For example, the immunoglobulin fusion proteins may be purified by passing a solution through a column which contains immobilized protein A or protein G which selectively binds the Fc portion of the fusion protein. See, for example, Reis, K. J., et al., J. Immunol. 132:3098-3102 (1984); PCT Application, Publication No. WO 87/00329. The fusion polypeptide may be eluted by treatment with a chaotropic salt or by elution with aqueous acetic acid (1 M).

Alternatively, ABO fusion polypeptides according to the invention can be chemically synthesized using methods known in the art. Chemical synthesis of polypeptides is described in, e.g., a variety of protein synthesis methods are common in the art, including synthesis using a peptide synthesizer. See, e.g., *Peptide Chemistry, A Practical Textbook*, Bodasnsky, Ed. Springer-Verlag, 1988; Merrifield, *Science* 232: 241-247 (1986); Barany, et al, *Intl. J. Peptide Protein Res.* 30: 705-739 (1987); Kent, *Ann. Rev. Biochem.* 57:957-989 (1988), and Kaiser, et al, *Science* 243: 187-198 (1989). The polypeptides are purified so that they are substantially free of chemical precursors or other chemicals using standard peptide purification techniques. The language "substantially free of chemical precursors or other chemicals" includes preparations of peptide in which the peptide is separated from chemical precursors or other chemicals that are involved in the synthesis of the peptide. In one embodiment, the language "substantially free of chemical precursors or other chemicals" includes preparations of peptide having less than about 30% (by dry weight) of chemical precursors or non-peptide chemicals, more preferably less than about 20% chemical precursors or non-peptide chemicals, still more preferably less than about 10% chemical precursors or non-peptide chemicals, and most preferably less than about 5% chemical precursors or non-peptide chemicals.

Chemical synthesis of polypeptides facilitates the incorporation of modified or unnatural amino acids, including D-amino acids and other small organic molecules. Replacement of one or more L-amino acids in a peptide with the corresponding D-amino acid isoforms can be used to increase the resistance of peptides to enzymatic hydrolysis, and to enhance one or more properties of biologically active peptides, i.e., receptor binding, functional potency or duration of action. See, e.g., Doherty, et al., 1993. *J. Med. Chem.* 36: 2585-2594; Kirby, et al., 1993. *J. Med. Chem.* 36:3802-3808; Morita, et al., 1994. *FEBS Lett.* 353: 84-88; Wang, et al., 1993. *Int. J. Pept. Protein Res.* 42: 392-399; Fauchere and Thiunieau, 1992. *Adv. Drug Res.* 23: 127-159.

Introduction of covalent cross-links into a peptide sequence can conformationally and topographically constrain the polypeptide backbone. This strategy can be used to develop peptide analogs of the fusion polypeptides with increased potency, selectivity and stability. Because the conformational entropy of a cyclic peptide is lower than its linear counterpart, adoption of a specific conformation may occur with a smaller decrease in entropy for a cyclic analog than for an acyclic analog, thereby making the free energy for binding more favorable. Macrocyclization is often accomplished by forming an amide bond between the peptide N- and C-termini, between a side chain and the N- or C-terminus [e.g., with $K_3Fe(CN)_6$ at pH 8.5] (Samson et al., *Endocrinology*, 137: 5182-5185 (1996)), or between two amino acid side chains. See, e.g., DeGrado, *Adv Protein Chem*, 39: 51-124 (1988). Disulfide bridges are also introduced into linear sequences to reduce their flexibility. See, e.g., Rose, et al., *Adv Protein Chem*, 37: 1-109 (1985); Mosberg et al., *Biochem Biophys Res Commun*, 106: 505-512 (1982). Furthermore, the replacement of cysteine residues with penicillamine (Pen, 3-mercapto-(D) valine) has been used to increase the selectivity of some opioid-receptor interactions. Lipkowski and Can, *Peptides: Synthesis, Structures, and Applications*, Gutte, ed., Academic Press pp. 287-320 (1995).

Composition and Kits

Also included in the invention are compositions containing at least two blood group antigens (e.g., ABO oligosaccharides) were each blood group antigen is expressed on a different core saccharide chain type. The blood group antigen is an A antigen, a B Antigen or an H antigen. The core saccharide chain type is a type 1, a type 2, a type 3 or a type 4. The composition contains 2, 3, 4, 5, 6, 7, 8 or more different blood group antigens.

Exemplary blood groups antigens include those recited above.

Optionally, the ABO oligosaccharides or the ABO fusion proteins are linked to a solid support. The linkage is covalent. Alternatively, the linkage is non-covalent.

The solid support can be, for example, a bead, resin, membrane or disk, or any solid support material suitable for methods of the invention. Preferably, the solid support is a bead, e.g., microbead. The size of the bead is not critical. Typically, the bead is at least 1 to 50 μm in diameter with a particle size of 1 to 10 μm m being preferred. Most preferably the beads had a diameter of about 4-10 μm. For example, 2, 3, 4, 5, 10, 15, 20, 25, 30, 40 or 50 μm diameters.

The bead may be made of metal compounds, silica, latex, polymeric material, or a silica, latex or polymer nuclei coated with a metal or metal compound.

The solid support may carry functional groups such as hydroxyl, carboxyl, aldehyde or amino groups. The support may be positively charge, negatively charged or hydrophobic. Functionalized coated supports for use in the present invention may be prepared by modification of the support. For example uncoated supports may be treated with a polymer carrying one or such functional groups, such as polyurethane together with a polyglycol to provide hydroxyl groups or a cellulose derivative to provide hydroxyl groups, a polymer or copolymer of acrylic acid or methacrylic acid to provide carboxyl groups or an aminoalkylated polymer to provide amino groups. U.S. Pat. No. 4,654,267 describes the introduction of many surface coatings.

Preferably each different ABO oligosaccharides or ABO fusion protein is on a microbead of a different subtype. By subtype is meant that each microbead is detectably distinguishable such as by being of different sizes or having distinguishable labels. Such a use of differently sized microbeads or microbeads labeled such as with fluorophores allows the identification and/or separation of different beads by, for example, flow cytometry.

The invention further provides kit for the separation of identification of blood group reactive antibodies from a sample according to the methods of the invention. The kit contains a collection of microbeads of different subtypes each subtype is coated with a different ABO oligosaccharide or ABO fusion protein. Optionally the kit contains at least open labeled ligand capable of specifically binding an anti-blood group antigen antibody. For example, the ligand is an antibody or fragment thereof. The antibody or fragment thereof is a monoclonal antibody. Alternatively, the antibody or fragment thereof is a polyclonal antibody. Optionally, the antibody is a recombinant antibody. The antibody is an antibody fragment such as $F_{ab}$, $F_{ab'}$ and $F_{(ab')2}$ fragments. By "specifically bind" or "immunoreacts with" is meant that the antibody reacts with one or more antigenic determinants of the desired antigen and does not react (i.e., bind) with other polypeptides or binds at much lower affinity ($K_d > 10^{-6}$) with other polypeptides.

The antibody is a monovalent.

The label, is any substance used to facilitate identification and/or quantitation of a target. Labels are directly observed or measured or indirectly observed or measured. Labels include, but are not limited to, radiolabels that can be measured with radiation-counting devices; pigments, dyes or other chromogens that can be visually observed or measured with a spectrophotometer; spin labels that can be measured with a spin label analyzer; and fluorescent moieties, where the output signal is generated by the excitation of a suitable molecular adduct and that can be visualized by excitation with light that is absorbed by the dye or can be measured with standard fluorometers or imaging systems, for example. The label can be a luminescent substance such as a phosphor or fluorogen; a bioluminescent substance; a chemiluminescent substance, where the output signal is generated by chemical modification of the signal compound; a metal-containing substance; or an enzyme, where there occurs an enzyme-dependent secondary generation of signal, such as the formation of a colored product from a colorless substrate. The label may also take the form of a chemical or biochemical, or an inert particle, including but not limited to colloidal gold, microspheres, quantum dots, or inorganic crystals such as nanocrystals or phosphors (see, e.g., Beverloo, et al., Anal. Biochem. 203, 326-34 (1992)). The term label can also refer to a "tag" or hapten that can bind selectively to a labeled molecule such that the labeled molecule, when added subsequently, is used to generate a detectable signal. For instance, one can use biotin, iminobiotin or desthiobiotin as a tag and then use an avidin or streptavidin conjugate of horseradish peroxidase (HRP) to bind to the tag, and then use a chromogenic substrate (e.g., tetramethylbenzidine) or a fluorogenic substrate such as Amplex Red or Amplex Gold (Molecular Probes, Inc.) to detect the presence of HRP Similarly, the tag can be a hapten or antigen (e.g., digoxigenin), and an enzymatically, fluorescently, or radioactively labeled antibody can be used to bind to the tag. Numerous labels are known by those of skill in the art and include, but are not limited to, particles, fluorescent dyes, haptens, enzymes and their chromogenic, fluorogenic, and chemiluminescent substrates, and other labels that are described in the Molecular Probes Handbook Of Fluorescent Probes And Research Chemicals by Richard P. Haugland, 6th Ed., (1996), and its subsequent 7th edition and 8th edition updates issued on CD Rom in November 1999 and May 2001, respectively, the contents of which are incorporated by reference, and in other published sources.

A fluorophore is any chemical moiety that exhibits an absorption maximum beyond 280 nm, and when covalently attached to a labeling reagent retains its spectral properties. Fluorophores include, without limitation; a pyrene (including any of the corresponding derivative compounds disclosed in U.S. Pat. No. 5,132,432), an anthracene, a naphthalene, an acridine, a stilbene, an indole or benzindole, an oxazole or benzoxazole, a thiazole or benzothiazole, a 4-amino-7-nitrobenz-2-oxa-1,3-diazole (NBD), a cyanine (including any corresponding compounds in U.S. Ser. Nos. 09/968,401 and 09/969,853), a carbocyanine (including any corresponding compounds in U.S. Ser. Nos. 09/557,275; 09/969,853 and 09/968,401; U.S. Pat. Nos. 4,981,977; 5,268,486; 5,569,587; 5,569,766; 5,486,616; 5,627,027; 5,808,044; 5,877,310; 6,002,003; 6,004,536; 6,008,373; 6,043,025; 6,127,134; 6,130,094; 6,133,445; and publications WO 02/26891, WO 97/40104, WO 99/51702, WO 01/21624; EP 1 065 250 A1), a carbostyryl, a porphyrin, a salicylate, an anthranilate, an azulene, a perylene, a pyridine, a quinoline, a borapolyazaindacene (including any corresponding compounds disclosed in U.S. Pat. Nos. 4,774,339; 5,187,288; 5,248,782; 5,274, 113; and 5,433,896), a xanthene (including any corresponding compounds disclosed in U.S. Pat. Nos. 6,162,931; 6,130, 101; 6,229,055; 6,339,392; 5,451,343 and U.S. Ser. No. 09/922,333), an oxazine (including any corresponding compounds disclosed in U.S. Pat. No. 4,714,763) or a benzoxazine, a carbazine (including any corresponding compounds disclosed in U.S. Pat. No. 4,810,636), a phenalenone, a coumarin (including an corresponding compounds disclosed in U.S. Pat. Nos. 5,696,157; 5,459,276; 5,501,980 and 5,830, 912), a benzofuran (including an corresponding compounds disclosed in U.S. Pat. Nos. 4,603,209 and 4,849,362) and benzphenalenone (including any corresponding compounds disclosed in U.S. Pat. No. 4,812,409) and derivatives thereof. As used herein, oxazines include resorufins (including any corresponding compounds disclosed in U.S. Pat. No. 5,242, 805), aminooxazinones, diaminooxazines, and their benzo-substituted analogs.

Optionally, the kits contains a positive or negative control or both, instruction for using the kit (e.g., written, tape, VCR, CD-ROM, etc.), sample collection means. Sample collection means are well known to those skilled in the art. For example, the sample collection means is a CPT vacutainer tube.

The reagents are packaged in separate containers, e.g., ABO oligosaccharide or ABO fusion protein (either bound to a solid matrix or packaged separately with reagents for binding them to the matrix), a control reagent (positive and/or negative), and or a labeled ligand.

Methods of Treating or Preventing Antibody-Mediated Graft Rejection

Also included in the invention are methods of treating or preventing antibody mediated graft rejection (AMR), e.g., organ transplant rejection. Such transplants include but are not limited to kidney, liver, skin, pancreas, cornea, or heart.

AMR is meant to include any antibody mediated graft rejection by the recipient. The method includes contacting a biological sample from a subject with the ABO oligosaccharide or ABO fusion peptide of the invention. The biological sample is for example, blood, i.e., whole blood or plasma. The sample is known to or suspected of comprising an antibody, e.g., an anti-blood group antibody. In some aspects, the biological sample is withdrawn from the subject prior to contacting the sample with the ABO oligosaccharide or ABO fusion polypeptide. The biological sample is contacted with the ABO oligosaccharide or ABO fusion peptide under conditions to allow formation of an ABO oligosaccharide or ABO fusion peptide-anti-blood group antibody complex. The ABO oligosaccharide or ABO fusion peptide-complex, if present is separated from the biological sample to eliminate the anti-blood group antibodies and the biological sample is reinfused into the subject.

AMR is also treated or prevented by administering to a subject an ABO fusion polypeptide of the invention.

The subject can be e.g., any mammal, e.g., a human, a primate, mouse, rat, dog, cat, cow, horse, pig. The treatment is administered prior to the subject receiving an ABO-incompatible transplant. Alternatively, treatment is administered after a subject receives an ABO incompatible transplant.

The biological sample is contacted with the ABO oligosaccharide or ABO fusion protein by methods known to those skilled in the art. For example, plasmapheresis or extracorporeal immunoabsorption methods.

Essentially, any disorder, which is etiologically linked to an antibody mediated reaction, is considered amenable to prevention or to treatment. AMR is treated or prevent when the survival rate of the organ transplant is greater than an organ transplant not treated by the method of the invention. By survival rate of the transplant is meant the time before the transplant is rejected by the recipient. For example, AMR is treated or prevent when the transplant survives at least 1, 2, 4 or 8 weeks after transplantation. Preferably, the transplant survives 3, 6, 13 months. More preferably, the transplant survives 2, 3, 5 or more years.

Methods of Removing Anti-Blood Group Antibodies from a Sample

Also included in the invention are methods of removing or depleting anti-blood group antibodies from a sample. The sample is a biological fluid such as blood or plasma. Alternatively, the sample is a biological tissue, such as heart tissue, liver tissue, skin, or kidney tissue. The method includes contacting a sample with the ABO oligosaccharide or ABO fusion peptide of the invention. The sample is contacted with the ABO fusion peptide under conditions to allow formation of an ABO oligosaccharide or ABO fusion peptide-anti-blood group antibody complex. The ABO fusion peptide-antibody complex, if present is separated from the biological sample to remove or deplete the anti-blood group antibodies.

This method is useful to produce universal donor plasma.

Methods of Blood Typing

Also included in the invention are methods of blood typing a subject. A subject is blood typed by contacting a sample, e.g., plasma or whole blood from a subject with a collection of microbeads of different subtypes. Each subtype contains a different blood group antigen. The blood group antigens are expressed on different core saccharide chain types. The microbeads and sample are contacted, e.g. incubated, for a sufficient amount a time to allow the anti-blood group antibodies present in the sample to bind, e.g. form an blood group antigen-antibody complex, to the blood group antigens on the microbeads.

After complex formation the sample is optionally washed one or more times to remove unbound plasma components. Alternatively unbound plasma components are separated from the micobeads by performing a separation step in which the microbead are removed from the sample. Separation is performed by methods known in the art such as centrifugation. The microbeads are further contacted with a labeling reagent that specifically binds the anti-blood group antibodies that is bound to microbead. The microbeads are optionally washed one or more times to remove unbound labeling reagent. The presence or absence of the anti-blood group antibodies in the sample is then determined by detecting the labeling reagent. Detection is done my methods known in the art such as by flow cytometry or luminex The invention also provides for the detection of multiple anti-blood group antibodies in a sample. By multiple anti-blood group antibodies it is meant not only antibodies specific for each of the blood groups (i.e, ABH) but antibodies specific for blood group antigens of different oligosaccharide core chain types. Multiple targets are identified by contacting the biological sample with additional detection reagents followed by additional labeling reagent specific for the additional detection reagents using the method described above. For example, subsets of microbeads are prepared with distinct blood group antigens, e.g., blood group antigens that are distinguished by core oligosaccharide chain type. The microbead subsets are then added to the biological sample containing in a controlled ratio.

In alternative methods, subsets of labeling reagent are prepared with distinct labels, e.g., fluorophores that are distinguished by their emission spectra, e.g., one that emits in the green spectra and one that emits in the red spectra. The labeling reagent subsets are then added to the biological sample containing detection reagent-target complexes in a controlled ratio, e.g., two parts one labeling reagent (e.g., green emission) and one part the other labeling reagent (e.g., red emission) per target binding antibody. In this way the immunolabeled complexes can be used to detect a target. If another immuno-labeled complex were added to the sample the original target could be distinguished from the subsequently detected target.

Optionally, 2, 3, 4, 5, 6, 7, 8, 9, 10 or more blood group antigens are detected in a sample.

The sample is defined to include any material that may contain a blood group antigen. Typically, the sample is whole blood, sera or plasma.

The methods of the invention provide significant advantages over existing technology for blood typing. Specifically it allows for the detection of blood group antigen subtypes. Moreover, the methods allow for the qualification of the different blood group antigen subtypes in a sample to be determined.

The detection reagent is a compound that is capable of specifically binding the blood group antibodies bound to the microbead. The detection reagent is selected based on the desired target. The detection reagent is for example a polypeptide such as a target specific antibody or fragment thereof. As used herein, the term "antibody" refers to immunoglobulin molecules and immunologically active portions of immunoglobulin (Ig) molecules, i.e., molecules that contain an antigen binding site that specifically binds (immunoreacts with) an antigen. Such antibodies include, polyclonal, monoclonal, chimeric, single chain, $F_{ab}$, $F_{ab'}$ and $F_{(ab')2}$ fragments, and an $F_{ab}$ expression library. By "specifically bind" or "immunoreacts with" is meant that the antibody reacts with one or more antigenic determinants of the desired antigen and does not react (i.e., bind) with other polypeptides or binds at much lower affinity ($K_d > 10^{-6}$) with other polypeptides.

Monoclonal antibodies are particularly advantageous in practicing the methods of the present invention. Generally, monoclonal antibodies are more sensitive and specific than polyclonal antibodies. In addition, unlike polyclonal antibodies, which depend upon the longevity of the animal producing the antibody, the supply of monoclonal antibodies is indefinite. Polyclonal antibodies however, are useful when it is necessary to use antibodies with multiple isotypes, as generally most monoclonal antibodies are of the IgG1 subclass.

As used herein, the terms "immunological binding," and "immunological binding properties" refer to the non-covalent interactions of the type that occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides are quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473).

The invention will be further illustrated in the following non-limiting examples.

EXAMPLE 1

Construction of Expression Vectors

The expression vector carrying P-selectin glycoprotein ligand-1/mouse IgG$_{2b}$ (PSGL-1/mIgG$_{2b}$) cDNA was modified to contain an enterokinase (EK) cleavage site. This site can be used for down-stream release of the mouse IgG$_{2b}$ part.

The human blood group A gene was polymerase chain reaction (PCR) amplified off cDNA made from total RNA isolated from the MKN-45 cell line, and the blood group B gene was PCR amplified off cDNA made from total RNA isolated from the HuTu80 cell line.

The expression vectors used to generate stable transfectants are bidirectional, see schematic figures. The PSGL-1/mIgG$_{2b}$ expression vector has the EF1α promoter upstream of a polylinker, a splice donor and acceptor site, and the bidirectional poly(A) additional signal of SV40. Opposite in orientation to this transcription unit, using the poly(A) signals from the opposite direction, is a second transcription unit consisting of the HSV TK promoter followed by the coding sequence for puromycin acetyltransferase (PAC). Similarly, the β1,6GlcNAcT (core 2 enzyme) expression vector contains the EF1α promoter and the coding sequence for the neomycin resistance gene (Neo). The FUT2 (Se-gene) expression vector contains the same vector backbone, but with the CMV promoter and the neomycin resistance gene. The GalNAcT (A-gene) and the GalT (B-gene) expression vectors contain the CMV promoter and the blasictidin resistance gene (Bsd), the FUT1 (H-gene) and the β1,3GlcNAcT6 (core 3 enzyme) contain the CMV promoter and the zeocin resistance gene, and the GalT5 expression vector contain the CMV promoter and guanosine phosphoribosyl transferase gene (GPT).

The DNA sequences of the expression vectors were verified by automated sequencing.

EXAMPLE 2

Determination of PSGL-1/mIgG2b Expression Using Western Blotting and Indirect Immunofluorescence Expression of PSGL-1/mIgG$_{2b}$ in cell culture supernatants was determined using SDS-PAGE and Western blotting. Samples were run on 4-12% gradient gels (Invitrogen) in MES buffer (Invitrogen), and separated proteins were electrophoretically blotted onto nitrocellulose membranes (Invitrogen). Following blocking for 1 hour in 3% bovine serum albumin (BSA) in phosphate buffered saline (PBS) with 0.2% Tween 20, the membranes were probed for 1 hour at room temperature with a peroxidase-conjugated goat anti-mouse IgG Fc antibody (Sigma) diluted 1:4.000 in blocking buffer. The membranes were washed three times with PBS containing 0.2% Tween 20, and bound antibodies were visualized by chemiluminescence using the ECL kit (Amerham Biosciences), according to the manufacturer's instructions.

The cellular localization of PSGL-1/mIgG$_{2b}$ was determined by indirect immunofluorescence. CHO-K1 cells seeded on cover slips in six-well plates were transiently transfected with the PSGL-1/mIgG$_{2b}$ expression vector using Lipofectamine 2000 (Invitrogen), according to the manufacturer's instructions. Forty eight hours after transfection, cells were washed with PBS and fixed in 30% acetone/MeOH. Following blocking for 30 minutes in 1% BSA in PBS, PSGL-1/mIgG$_{2b}$ protein was detected using a FITC-conjugated goat anti-mouse IgG Fc antibody (Sigma) diluted 1:200 in blocking buffer. Cell nuclei were stained with 4,6-diamidino2-phenylindole (DAPI). The cover slips were mounted on slides with Vectashield Mounting Medium (Vector Laboratories). Slides were examined using a DMRXA microscope (Leica Corp.), and digitally imaged using a Hamamatsu C4880-40 CCD camera (Hamamatsu Photonics Norden AB), the Openlab software package (Improvision), and Adobe Photoshop software (see figure).

EXAMPLE 3

Adaptation of CHO-K1 Cells to Serum-Free Medium

The CHO-K1 cell line (ATCC CCL-61) was adapted to serum-free medium, Ex-cell 302 (JHR Bioscience, Inc), according to the manufacturer's instructions.

EXAMPLE 4

DNA Transfection and Clonal Selection

CHO-K1 cells adapted to serum-free medium were seeded in 75 cm$^2$ flasks and were transfected with the PSGL-1/mIgG$_{2b}$ expression vector using Lipofectamine 200 CD (Invitrogen), an animal origin-free formulation, according to the manufacturer's instructions. Forty eight hours after transfection, cells were incubated in puromycin-containing selection medium (6 μg/mL). The selection medium was changed every third day. After approx. 2 weeks, dead cells were removed using Dead Cell Removal MicroBeads (Miltenyi Biotech), according to the manufacturer's instructions. Live cells were single cell-cloned in 96-well plates, and expanded in selection medium for approx. 2 weeks. Cell culture supernatants were harvested and the concentration of hPSGL-1/mIgG$_{2b}$ was assessed by enzyme-linked immunosorbent assay (ELISA), see protocol below, using a goat anti-mouse IgG Fc antibody (Sigma). The cell clones with the highest hPSGL-1/mIgG$_{2b}$ expression were chosen for expansion.

EXAMPLE 5

Quantification of PSGL-1/mIgG$_{2B}$ Concentration in Supernatants Using ELISA

Cells were seeded in 25 cm$^2$ flasks (~1×10$^6$ cells/mL). Cell culture supernatants were harvested after 4 days. The concentration of PSGL-1/mIgG$_{2b}$ produced by the cell clones was assessed by enzyme-linked immunosorbent assay (ELISA). Ninety-six-well ELISA plates (Costar 3590, Corning) were coated for 2 hours with an affinity-purified goat anti-mIgG Fc antibody (Sigma) at a concentration of 10 µg/mL. The plates were blocked with 1% BSA in PBS for 2 hours. The supernatants containing PSGL-1/mIgG$_{2b}$ were serially diluted in blocking buffer and incubated for 2 hours. Following washing, the plates were incubated for 2 hours with a peroxidase-conjugated goat anti-mouse IgG Fc antibody (Sigma) diluted 1:4,000 in blocking buffer. Bound peroxidase-conjugated antibody was visualized with 3,3',5,5'-tetramethylbenzidine dihydrochloride (Sigma). The reaction was stopped with 2 M H$_2$SO$_4$ and the plates were read at 450 nm in an automated microplate reader (Bio-Tek Instruments). The PSGL-1/mIgG$_{2b}$ concentration was estimated using as a standard a dilution series of purified mIgG Fc fragments (Sigma). The highest producing cell clone (~25 µg/mL) was chosen for further transfections, as described below.

EXAMPLE 6

Generation of PSGL-1/mIgG$_{2B}$ Substituted with Blood Group A/B Type 3 Antigens The stable CHO-K1 cell line with the highest PSGL-1/mIgG$_{2b}$ expression was transfected with the FUT2 (Se-gene) expression vector, as described above, and selected in G418-containing medium (400 µg/mL). The cell clone with the highest relative number of blood group H type 3 antigens on PSGL-1/mIgG$_{2b}$ will be transfected with either the GalNAcT (A-gene) or GalT (B-gene) expression vectors, and selected in blasticidine-containing medium, to generate cell lines that produce blood group A and B, respectively, type 3 antigens on PSGL-1/mIgG$_{2b}$ (see transfection scheme).

EXAMPLE 7

Generation of PSGL-1/mIgG$_{2B}$ Substituted with Blood Group A/B Type 2 Antigens The stable CHO-K1 cell line with the highest PSGL-1/mIgG$_{2b}$ expression was transfected with the β1,6GlcNAcT1 (core 2 enzyme) and FUT1 (H-gene) expression vectors, and selected in medium containing G418 (400 µg/mL). The cell clone with the highest relative number of H type 2 antigens on PSGL-1/mIgG$_{2b}$ will be transfected with either the α1, 3 GalNAcT (A-gene) or α1, 3 GalT (B-gene) expression vectors, and selected in blasticidine-containing medium, to generate cell lines that produce blood group A and B, respectively, type 2 antigens on PSGL-1/mIgG$_{2b}$ (see transfection scheme).

EXAMPLE 8

Generation of PSGL-1/mIgG$_{2B}$ Substituted with Blood Group A/B Type 1 Antigens The cell clone with the highest relative number of blood group H type 3 antigens on PSGL-1/mIgG$_{2b}$ will be transfected with the β1,3GlcNAcT (core 3 enzyme) and GalT5 expression vectors, and selected in medium containing zeocin. The clone with the highest relative number of blood group H type 1 antigens on PSGL-1/mIgG$_{2b}$ will be transfected with either the α1,3 GalNAcT (A-gene) or α1,3 GalT (B-gene) expression vectors, and selected in blasticidine-containing medium, to generate cell lines that produce blood group A and B, respectively, type 1 antigens on PSGL-1/mIgG$_{2b}$ (see transfection scheme).

EXAMPLE 9

Purification of Recombinant hPSGL-1/EK/mIgG$_{2B}$

Cell culture supernatants will be cleared from debris by centrifugation, and passed through a column containing goat anti-mouse IgG (whole molecule) agarose (Sigma). After washing with PBS, bound hPSGL-1/EK/mIgG$_{2b}$ will be eluted with 3M NaSCN and dialyzed against distilled water. To remove low-molecular weight contaminants, hPSGL-1/EK/mIgG$_{2b}$ may be further purified by gel filtration on a HiPrep 16/60 Sephacryl S-200 HR column (Amersham Bioscience).

Covalent Coupling to Sepharose and Column Packing

Purified blood group A and B mucins will be covalent coupled to sepharose fast flow beads using standard bioconjugation chemistry. Following coupling, the sepharose will be packed in the plastic container constituting the actual column.

Adsorption Efficacy and Biocompatibility Testing of the Prototype Column.

The titres of anti-blood group ABO antibodies prior to and after adsorption of pooled blood group O plasma will be assessed by standard blood banking techniques including hemagglutination and the indirect anti-globulin test. Plasma proteins, including immunoglobulins (IgG, IgM and IgA), complement factors/fragments (C3, C3a, C3d, C4 and sC5b-9), immune complexes, and coagulation factors (FVIII, prothrombin, fibrinogen, fibrin degradation products) will all be measured by standard techniques. The specificities of adsorbed and eluted, and nonadsorbed ABO antibodies will be determined by ELISA using recombinant mucins carrying blood group A/B antigens on defined core saccharide chains or by a thin-layer chromatography-based overlay assay in which purified and structurally defined blood group A and B glycolipids are used.

EXAMPLE 10

Figure 5A:
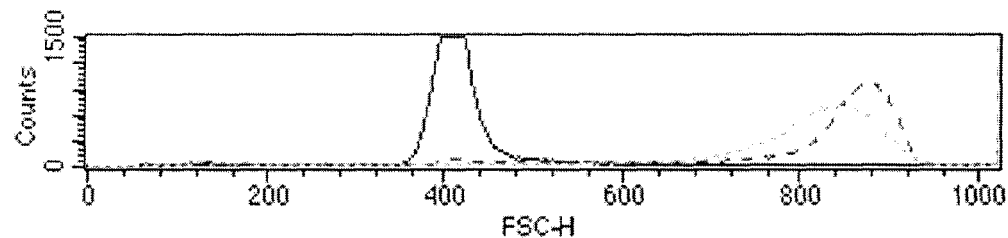
FIGS. 5A-D are graphs showing flow cytometry results from beads of 5 different sizes and colour intensities clearly showing that it is possible to use beads of many size-colour combinations. Using combinations of the above shown sizes and colours it would be possible to make a mixture of up to 25 different beads each expressing a unique blood group antigen.
Figure 5B:
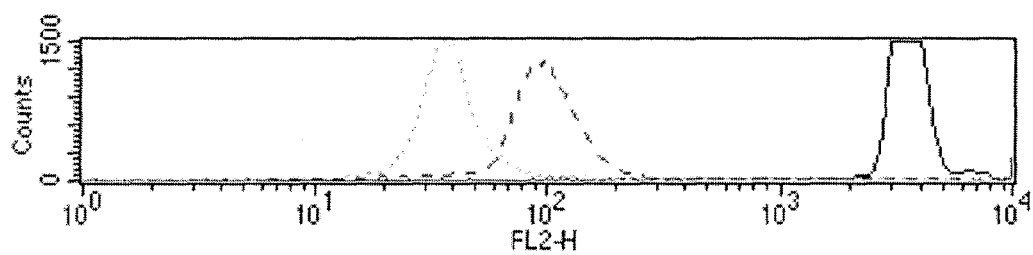
Figure 5C:
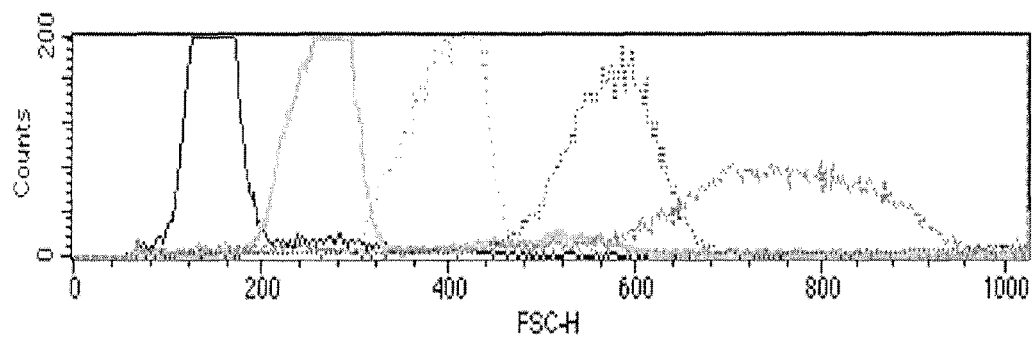
Figure 5D:
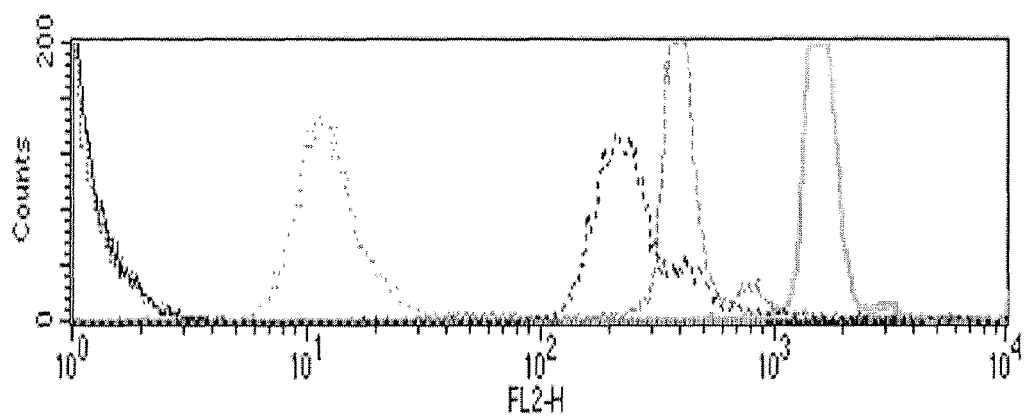
Figure 6:
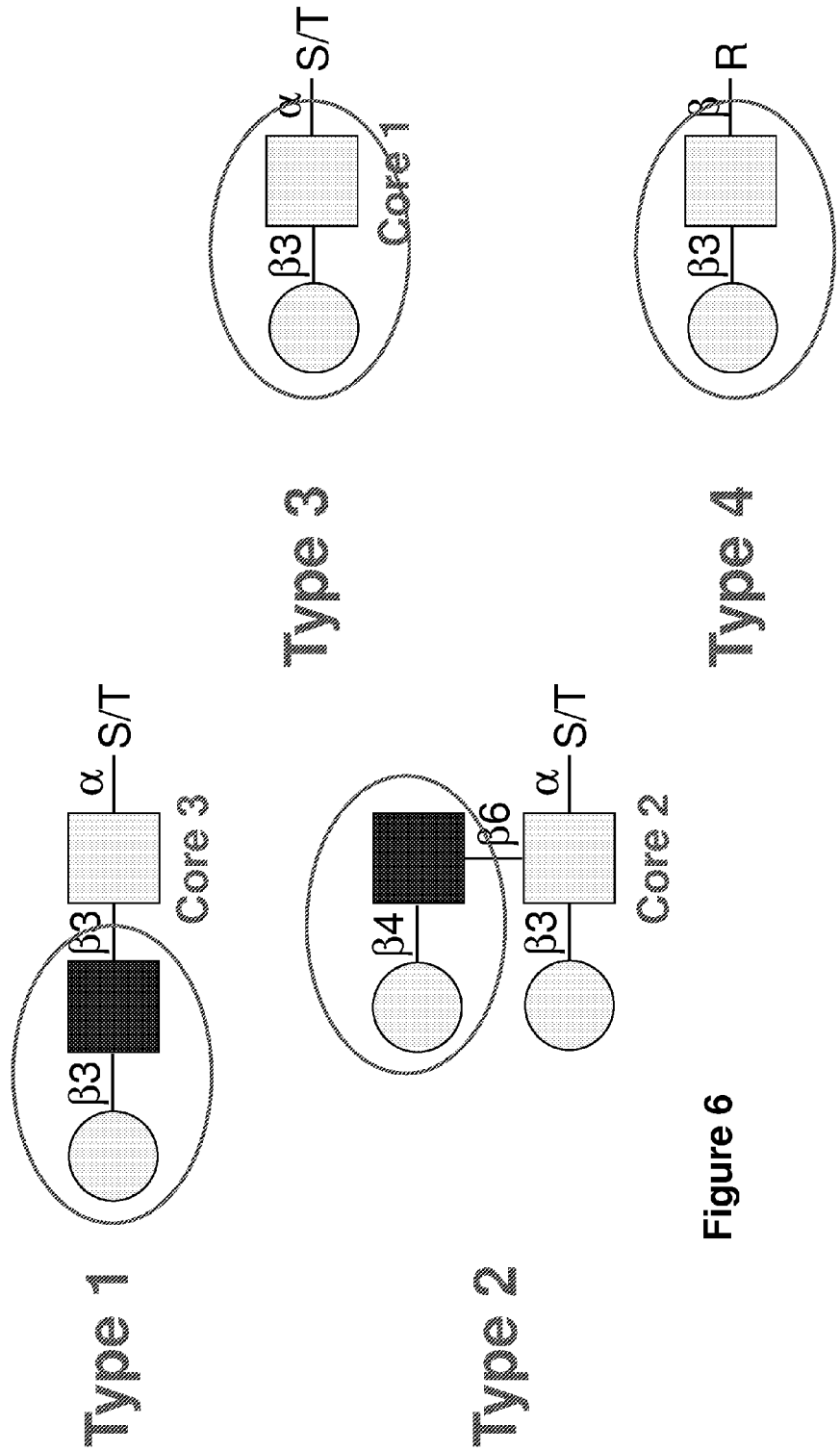
FIG. 6 is a schematic representation of outer core structures of blood group antigen.
Figure 7:
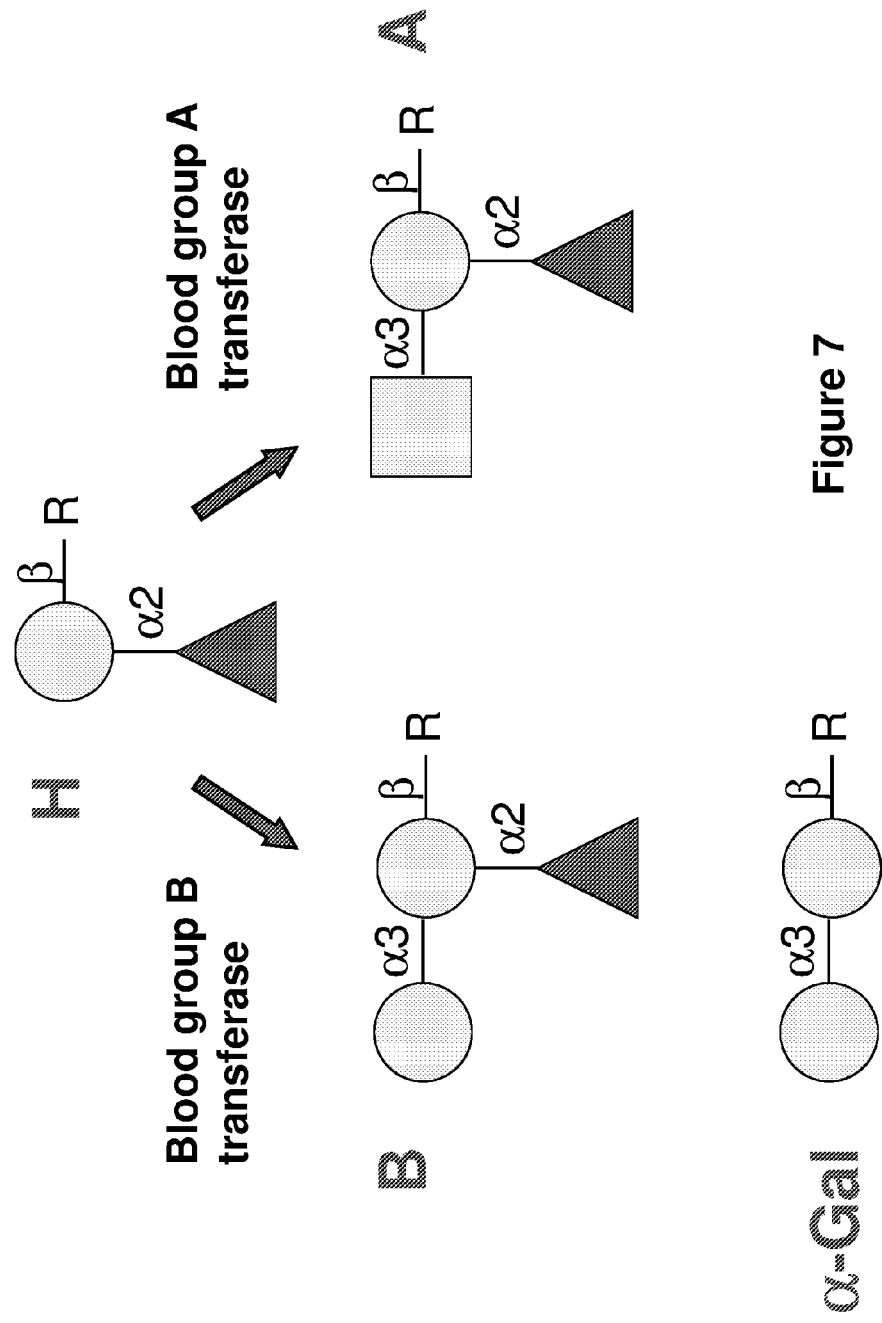
FIG. 7 is a schematic representation of blood group ABH antigens.
Figure 8:
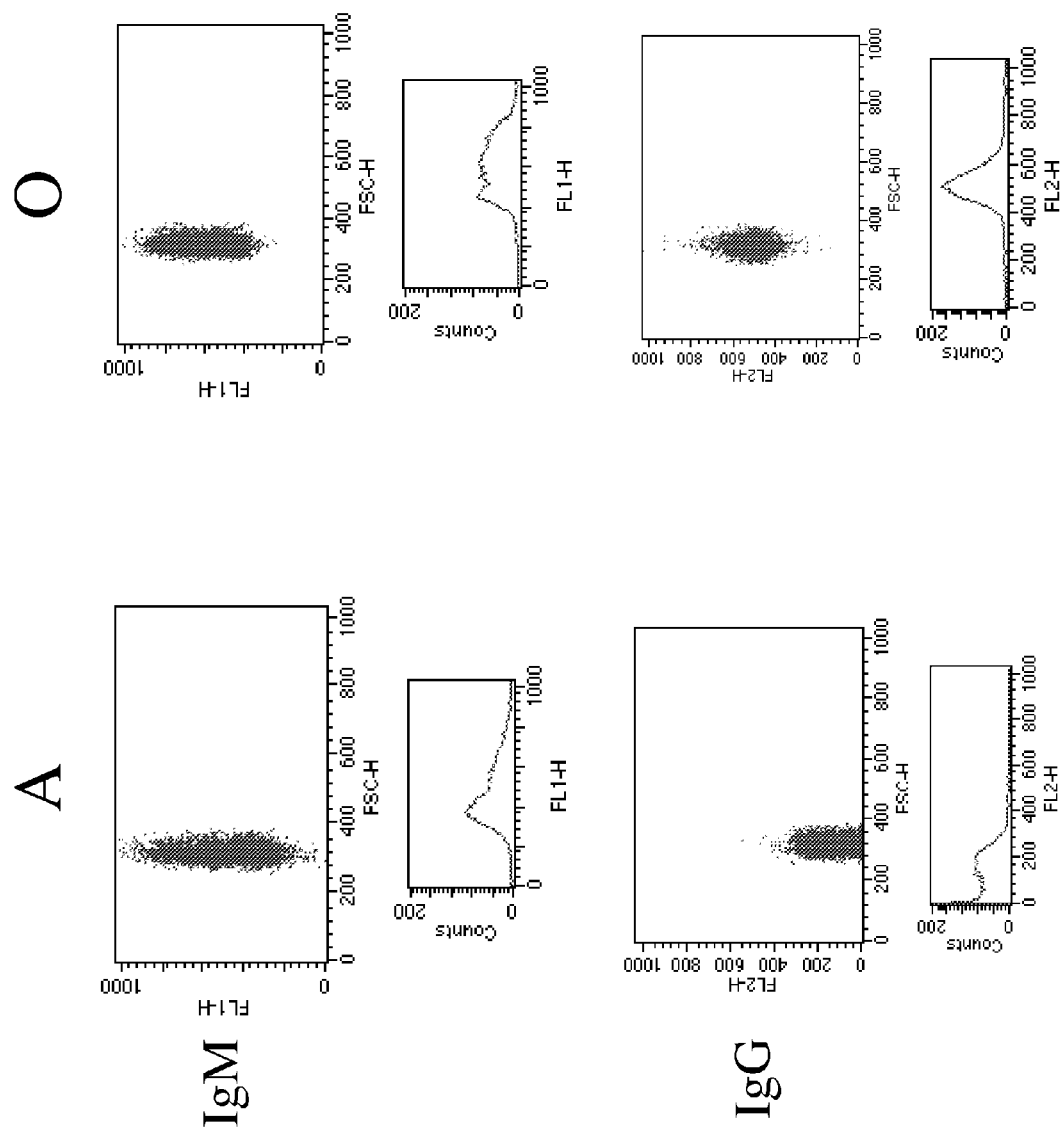
FIG. 8 is a graphical representation of flow cytometry results identifying anti-blood group antibodies in serum.
Figure 9:
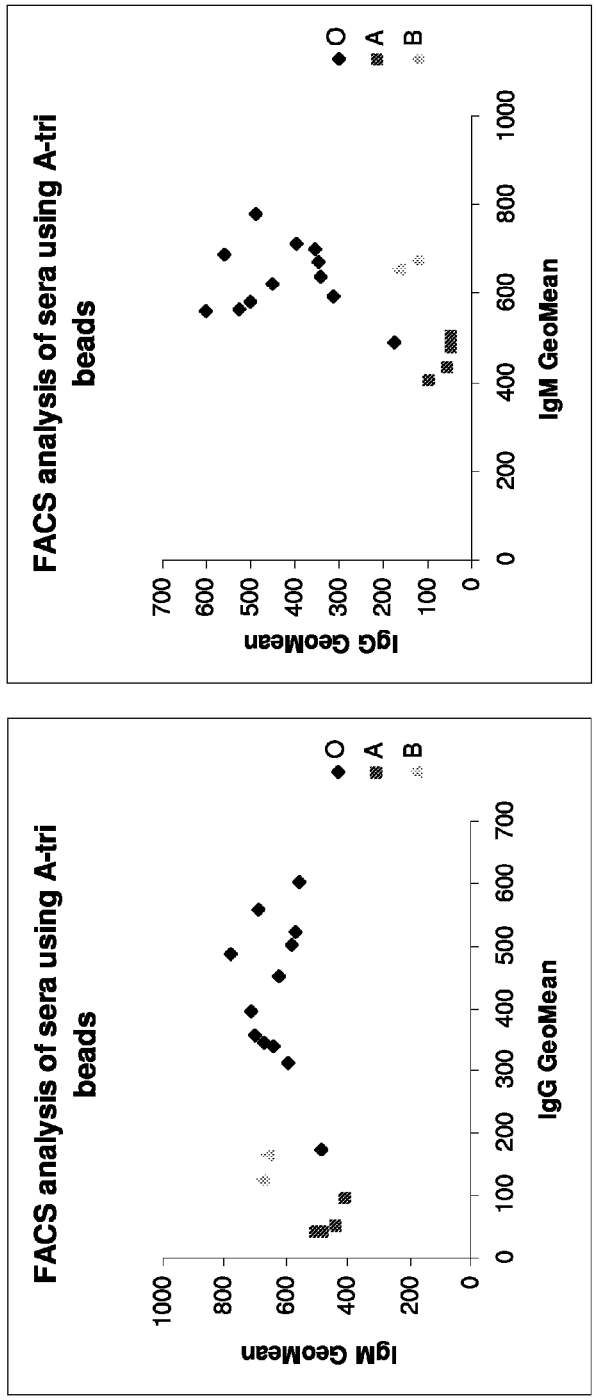
FIG. 9 is a series of scatter plots showing IgG and IgM blood group A antibodies in serum from A, B, and O individuals.

Production of Beads of Different Sizes and Colours for Determination of Antibody Titers Beads of different sizes and colours were produced micromod Partikeltechnologie GmbH in Rostock, Germany and conjugated to blood group antigens of different types. Beads were analyzed by flow cytometry and showed good resolution both regarding size and colour (see FIG. 5). Using this method it is possible to use a mixture of a large number of beads conjugated were each size-colour intensity combination represents a specific blood group antigen expressed on a specific core structure.

EXAMPLE 11

Detection of Blood Group Antibodies

Serum samples are diluted 1:10 in PBS with 0.5% human albumin and mixed with latex microbead (4.6 μm; 18 μg dry weight) carrying blood group antigen oligosaccharides. Serum and microbeads are incubated at room temperature for 30 minutes and then washed with 0.5% HAS/PBS. FITC labeled anti-human IgM and PE labeled IgG is added to the washed microbeads and analyzed by flow cytometry.

REFERENCES

1) L Rydberg *Transfus Med* 2001; 11:325-342
2) K I Welsh, M van Dam, C G Koffman Transplant Proc 1987; 19:4565-4567
3) K Tanabe, K Takahashi, T Agishi, H Toma, K Ota *Transfus Sci* 1996; 17: 455-462
4) K Takahashi *Acomodation in AB0-incompatible kidney transplantation*: Elsevier, Amsterdam; 2004.
5) M D Stegall, P G Dean, J M Gloor *Transplantation* 2004; 78: 635-640
6) C J Sonnenday, D S Warren, M Cooper, et al *Am J Transplant* 2004; 4: 1315-1322
7) G Tyden, G Kumlien, H Genberg, J Sandberg, T Lundgren, I Fehrman *Am J Transplant* 2005; 5: 145-148
8) D S Warren, A A Zachary, C J Sonnenday, et al *Am J Transplant* 2004; 4: 561-568
9) H Clausen, S Hakomori *Vox Sang* 1989; 56: 1-20
10) R Oriol, J Danilovs, H R Hawkins *A J Hum Genet* 1981; 33
11) F Yamamoto *Immunohematol* 2004; 20: 3-22
12) K Furukawa, M J Mattes, K O Lloyd *J Immunol* 1995; 135: 4090-4094
13) M Mammen, S Choi, G Whitesides *Angew Chem Int Ed* 1998; 37: 2754-2794
14) J C Löfling, E Hauzenberger, J Holgersson *Glycobiology* 2002; 12:173-182
15) J Liu, A Gustafsson, M E Breimer, A Kussak, J Holgersson *Glycobiology* 2005; 15: 571-583
16) J Liu, A Weintraub, J Holgersson *Xenotransplantation* 2003; 10:149-163
17) J Liu, Y Qian, J Holgersson *Transplantation* 1997; 63: 1673-1682
18) L Rydberg, A Bengtsson, O Samuelsson, K Nilsson, M E Breimer *Transpl Int* 2005; 17: 666-672
19) G Tyden, G Kumlien, I Fehrman Transplantation 2003; 76: 730-1
20) G Tyden, G Kumlien, H Genberg, J Sandberg, T Lundgren, I Fehrman *Am J Transplant*. 2005; 5: 145-8.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

---

What is claimed is:

1. A method for determining the presence of anti-blood group antigen reactive antibodies in serum of a subject, said method comprising:

a) providing a collection of blood group antigens coated onto a solid surface, wherein the collection of blood group antigens comprises one or more blood group antigens selected from the group consisting of:

A type 1 GalNAcα1,3(Fucα1,2)Galβ1,3GlcNAcβ1-R,
   A type 2 GalNAcα1,3(Fucα1,2)Galβ1,4GlcNAcβ1-R,
   A type 3 GalNAcα1,3(Fucα1,2)Galβ1,3GalNAcα1-R,
   A type 4 GalNAcα1,3(Fucα1,2)Galβ1,3GalNAcβ1-R,
   B type 1 Galα1,3(Fucα1,2)Galβ1,3GlcNAcβ1-R,
   B type 2 Galα1,3(Fucα1,2)Galβ1,4GlcNAcβ1-R,
   B type 3 Galα1,3(Fucα1,2)Galβ1,3GalNAcα1-R, and B type 4 Galα1,3(Fucα1,2)Galβ1,3GalNAcβ1-R;
wherein the blood group antigens are linked to the solid surface, and R represents the point of attachment to the solid surface;

b) adding said serum from said subject to said blood group antigen coated solid surface;

c) incubating said serum and said blood group antigen coated solid surface for sufficient time for anti-blood group antigen reactive antibodies in said serum to bind to said blood group antigens;

d) removing components in said serum which do not specifically bind to said blood group antigen coated solid surface;

e) incubating said solid surface with ligands capable of specifically binding to said anti-blood group antigen reactive antibodies bound to said blood group antigens; wherein said ligands are labeled with different labels such that one blood group antigen differs from at least one other blood group antigen by being labeled with said differently labeled ligands;

f) removing said labeled ligands that are not bound to said anti-blood group antigen reactive antibodies; and g) detecting the presence of said differently labeled ligands bound to said anti-blood group antigen reactive antibodies to determine the presence or absence of said reactive antibodies.

2. The method of claim 1, wherein the labeled ligands are labeled with fluorescent labels.

3. The method of claim 1, wherein said labeled ligands are antibodies or binding fragments thereof.

4. The method of claim 3, wherein said labeled ligands are monovalent antibody fragments.

5. The method of claim 4, wherein said monovalent antibody fragments are Fab or Fab' fragments.

6. The method of claim 5, wherein said Fab or Fab' fragments are selected from the group consisting of an anti-Fc antibody fragment, an anti-kappa light chain antibody fragment, an anti-lambda light chain antibody fragment, and a single chain antibody fragment.

7. The method of claim 1, wherein the collection of blood group antigens comprises at least one blood group antigen selected from the group consisting of:
A type 1 GalNAcα1,3(Fucα1,2)Galβ1,3GlcNAcβ1-R,
A type 2 GalNAcα1,3(Fucα1,2)Galβ1,4GlcNAcβ1-R,
A type 3 GalNAcα1,3(Fucα1,2)Galβ1,3GalNAcα1-R, and
A type 4 GalNAcα1,3(Fucα1,2)Galβ1,3GalNAcβ1-R.

8. The method of claim 1, wherein the collection of blood group antigens comprises at least one blood group antigen selected from the group consisting of:
B type 1 Galα1,3(Fucα1,2)Galβ1,3GlcNAcβ1-R,
B type 2 Galα1,3(Fucα1,2)Galβ1,4GlcNAcβ1-R,
B type 3 Galα1,3(Fucα1,2)Galβ1,3GalNAcα1-R, and
B type 4 Galα1,3(Fucα1,2)Galβ1,3GalNAcβ1-R.

9. The method according to claim 1, wherein the collection of blood group antigens comprises at least two blood group antigens selected from the group consisting of:
A type 1 GalNAcα1,3(Fucα1,2)Galβ1,3GlcNAcβ1-R,
A type 2 GalNAcα1,3(Fucα1,2)Galβ1,4GlcNAcβ1-R,
A type 3 GalNAcα1,3(Fucα1,2)Galβ1,3GalNAcα1-R, and
A type 4 GalNAcα1,3(Fucα1,2)Galβ1,3GalNAcβ1-R.

10. The method according to claim 1, wherein the collection of blood group antigens comprises at least three blood group antigens selected from the group consisting of:
A type 1 GalNAcα1,3(Fucα1,2)Galβ1,3GlcNAcβ1-R,
A type 2 GalNAcα1,3(Fucα1,2)Galβ1,4GlcNAcβ1-R,
A type 3 GalNAcα1,3(Fucα1,2)Galβ1,3GalNAcα1-R, and
A type 4 GalNAcα1,3(Fucα1,2)Galβ1,3GalNAcβ1-R.

11. The method according to claim 1, wherein the collection of blood group antigens comprises at least four blood group antigens selected from the group consisting of:
A type 1 GalNAcα1,3(Fucα1,2)Galβ1,3GlcNAcβ1-R,
A type 2 GalNAcα1,3(Fucα1,2)Galβ1,4GlcNAcβ1-R,
A type 3 GalNAcα1,3(Fucα1,2)Galβ1,3GalNAcα1-R, and
A type 4 GalNAcα1,3(Fucα1,2)Galβ1,3GalNAcβ1-R.

12. The method according to claim 1, wherein the collection of blood group antigens comprises at least two blood group antigens selected from the group consisting of:
B type 1 Galα1,3(Fucα1,2)Galβ1,3GlcNAcβ1-R,
B type 2 Galα1,3(Fucα1,2)Galβ1,4GlcNAcβ1-R,
B type 3 Galα1,3(Fucα1,2)Galβ1,3GalNAcα1-R, and
B type 4 Galα1,3(Fucα1,2)Galβ1,3GalNAcβ1-R.

13. The method according to claim 1, wherein the collection of blood group antigens comprises at least three blood group antigens selected from the group consisting of:
B type 1 Galα1,3(Fucα1,2)Galβ1,3GlcNAcβ1-R,
B type 2 Galα1,3(Fucα1,2)Galβ1,4GlcNAcβ1-R,
B type 3 Galα1,3(Fucα1,2)Galβ1,3GalNAcα1-R, and
B type 4 Galα1,3(Fucα1,2)Galβ1,3GalNAcβ1-R.

14. The method according to claim 1, wherein the collection of blood group antigens comprises at least four blood group antigens selected from the group consisting of:
B type 1 Galα1,3(Fucα1,2)Galβ1,3GlcNAcβ1-R,
B type 2 Galα1,3(Fucα1,2)Galβ1,4GlcNAcβ1-R,
B type 3 Galα1,3(Fucα1,2)Galβ1,3GalNAcα1-R, and
B type 4 Galα1,3(Fucα1,2)Galβ1,3GalNAcβ1-R.

15. The method according to claim 1, where in the solid surface is a microtiter plate, resin, nitrocellulose, or nylon.

* * * * *

SEQUENCE LISTING

```
<160> NUMBER OF SEQ ID NOS: 2

<210> SEQ ID NO 1
<211> LENGTH: 15
<212> TYPE: DNA
<213> ORGANISM: Artificial Sequence
<220> FEATURE:
<223> OTHER INFORMATION: synthetic enzyme cleavage site

<400> SEQUENCE: 1
gacgatgacg ataag                                               15

<210> SEQ ID NO 2
<211> LENGTH: 5
<212> TYPE: PRT
<213> ORGANISM: Artificial Sequence
<220> FEATURE:
<223> OTHER INFORMATION: synthetic enzyme cleavage site

<400> SEQUENCE: 2

Asp Asp Asp Asp Lys
1               5
```